US008106010B2

(12) United States Patent
Maik-Rachline et al.

(10) Patent No.: US 8,106,010 B2
(45) **Date of Patent: *Jan. 31, 2012**

(54) VARIANTS OF PIGMENT EPITHELIUM DERIVED FACTOR AND USES THEREOF

(75) Inventors: Galia Maik-Rachline, Kfar Saba (IL); Rony Seger, Yavne (IL)

(73) Assignee: Yeda Research and Development Co. Ltd. at the Weizmann Institute of Science, Rehovot (IL)

( * ) Notice: Subject to any disclaimer, the term of this patent is extended or adjusted under 35 U.S.C. 154(b) by 538 days.

This patent is subject to a terminal disclaimer.

(21) Appl. No.: 12/093,576

(22) PCT Filed: Nov. 14, 2006

(86) PCT No.: PCT/IL2006/001314

§ 371 (c)(1),
(2), (4) Date: May 13, 2008

(87) PCT Pub. No.: WO2007/054949

PCT Pub. Date: May 18, 2007

(65) Prior Publication Data

US 2008/0274967 A1 Nov. 6, 2008

Related U.S. Application Data

(60) Provisional application No. 60/735,875, filed on Nov. 14, 2005.

(51) Int. Cl.

| | |
|---|---|
| ***A61K 38/04*** | (2006.01) |
| *C12N 15/63* | (2006.01) |
| *C12P 21/06* | (2006.01) |
| *C07K 14/47* | (2006.01) |

(52) U.S. Cl. .................. 514/13.3; 514/44 R; 424/93.21; 435/69.1; 435/320.1; 435/325; 530/350; 530/387.3; 536/23.1; 536/23.5

(58) Field of Classification Search ........................ None
See application file for complete search history.

(56) References Cited

U.S. PATENT DOCUMENTS

| | | | |
|---|---|---|---|
| 4,816,567 | A | 3/1989 | Cabilly |
| 5,840,686 | A | 11/1998 | Chander |
| 6,319,687 | B1 | 11/2001 | Chander |
| 6,821,775 | B1 | 11/2004 | Kovesti |
| 6,919,309 | B2 | 7/2005 | Bouck |
| 7,105,496 | B2 | 9/2006 | Bouck |
| 2003/0158112 | A1 | 8/2003 | Campochiaro |
| 2003/0216286 | A1 | 11/2003 | Bouck |
| 2004/0014664 | A1 | 1/2004 | Bouck |
| 2005/0148508 | A1 | 7/2005 | Shaltiel |
| 2005/0222031 | A1 | 10/2005 | Yamagishi et al. |

FOREIGN PATENT DOCUMENTS

| | | | |
|---|---|---|---|
| WO | 93/24529 | A1 | 12/1993 |
| WO | 95/33480 | A1 | 12/1995 |
| WO | 03/059248 | A1 | 7/2003 |
| WO | 03/080648 | A1 | 10/2003 |
| WO | 2004/028559 | A1 | 4/2004 |
| WO | 2005/041887 | A1 | 5/2005 |
| WO | 2006/054278 | A1 | 5/2006 |

OTHER PUBLICATIONS

Pignolo et al, The Journal of Biological Chemistry, 1993, vol. 268, pp. 8949-8957.*
Verma et al. Nature, 1997, vol. 389, pp. 239-242.*
Anderson, W. (Nature, 1998, vol. 392, pp. 25-30.*
Rubanyi, biol. Aspects Med. (2001) 22:113-142.*
Juengst , British Medical Journal (2003) vol. 326, pp. 1410-1411.*
Vosloglou-Nomikos et al, Clinical Cancer Research, Sep. 15, 2003, vol. 9, pp. 4227-4239.*
Becerra, S. Patricia et al., "Overexpression of fetal human pigment epithelium-derived factor in *Escherichia coli*. A functionally active neurotrophic factor," J. Biol. Chem. 268(31): 23148-23156 (1993).
Berns, Kenneth I. et al., "Adenovirus and Adeno-Associated Virus as Vectors for Gene Therapy," Ann. N.Y. Acad. Sci. 772:95-104 (1995).
Federoff, Howard J. et al., "Expression of nerve growth factor in vivo from a defective herpes simplex virus 1 vector prevents effects of axotomy on sympathetic ganglia," Proc. Natl. Acad. Sci. USA 89(5):1636-1640 (1992).
Fink, D. J. et al., "Gene Transfer to Neurons Using Herpes Simplex Virus-Based Vectors," Ann. Rev. Neurosci. 19:265-287 (1996).
Huse, William D. et al., "Generation of a large combinatorial library of the immunoglobulin repertoire in phage lambda," Science 246(4935):1275-1281 (1989).
Kohler, G. et al., "Derivation of specific antibody-producing tissue culture and tumor lines by cell fusion," Eur. J. Immunol 6(7):511-519 (1976).
Maik-Rachline, Galia et al., "Extracellular phosphorylation converts pigment epithelium-derived factor from a neurotrophic to an antiangiogenic factor," Blood 105(2):670-678 (2005).
Maik-Rachline, Galia et al., "Variable phosphorylation states of pigment-epithelium-derived factor differentially regulate its function," Blood 107(7):2745-2752 (2006).
Mural, Richerd J. et al., "A comparison of whole-genome shotgun-derived mouse chromosome 16 and the human genome," Science 296(5573):1661-1671 (2002).
Passaniti, Antonino et al., "A simple, quantitative method for assessing angiogenesis and antiangiogenic agents using reconstituted basement membrane, heparin, and fibroblast growth factor," Lab. Invest. 67(4):519-528 (1992).
Shirozu, Michio et al., "Characterization of novel secreted and membrane proteins isolated by the signal sequence trap method," Genomics 37(3)273-280 (1996).

(Continued)

*Primary Examiner* — Bridget E Bunner
*Assistant Examiner* — Fozia Hamud
(74) *Attorney, Agent, or Firm* — Rodney J. Fuller; Fennemore Craig, P.C.

(57) ABSTRACT

The present invention relates to anti-angiogenic variants of pigment epithelium derived factor (PEDF) comprising a plurality of altered phosphorylation sites, polynucleotides encoding same and uses thereof. In particular, the PEDF variants of the present invention provide superior anti-angiogenic activity and high neurotrophic activity and are useful in treating diseases associated with neovascularization and with neurodegenerative conditions.

26 Claims, 9 Drawing Sheets

OTHER PUBLICATIONS

Singh, Vijay K. et al., "Structural and comparative analysis of the mouse gene for pigment epithelium-derived factor (PEDF)," Molecular Vision 4:7 (1998).

Tombran-Tink, Joyce, "The neuroprotective and angiogenesis inhibitory serpin, PEDF: New insight into phylogeny, function, and signaling," Frontiers in Bioscience 10(S):2131-2149 (2005).

Ward E. Sally et al., "Binding activities of a repertoire of single immunoglobulin variable domains secreted from *Escherichia coli*," Nature 341(6242):544-546 (1989).

Database Uniport [online] Jul. 15, 1998 "Recname: Full=pigment epithelium-derived factor; short=PEDF; Altname: Full=Serpin F1; Altname: Full=stromal cell-derived factor 3; Short=SDF-3; Altname: Full=Caspin; Flags;Precurser;" retrieved from EBI accession No. UNIPOPRT:P97298.

Database Uniport [online] May 10, 2005 "Subname:Full=Serine (or cysteine proteinase inhibitor, clade F, member 1; Subname:Full=Serine (or cysteine) peptidase inhibitor, clade F, member 1, isoform CRA_a;" XP002573504 retrieved from EBI accession No. Q5ND38.

International Search Report and Written Opinion of the International Searching Authority of PCT/IL2006/001314 mailed Mar. 25, 2009.

International Preliminary Report on Patentability of PCT/IL2006/001314 mailed Aug. 13, 2009.

Supplementary European Search Report of EP 06809870 completed Mar. 23, 2010.

* cited by examiner

FIG. 1A PKA phos
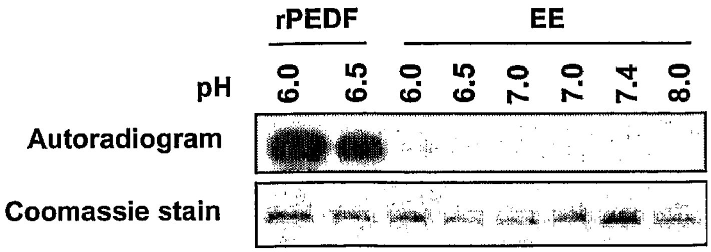
FIG. 1B PKA phos
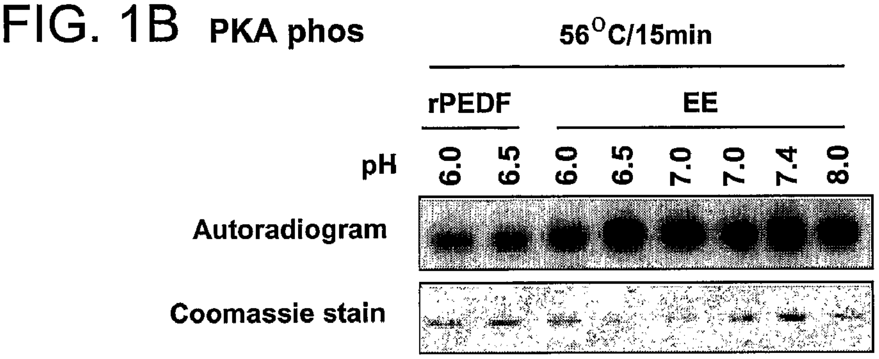
FIG. 1C PKA phos
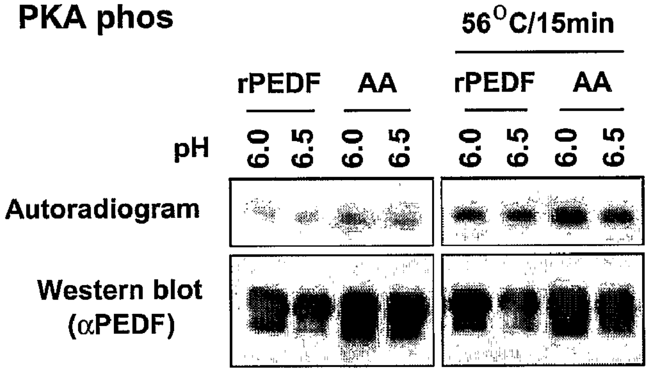
FIG. 1D CK2 phos
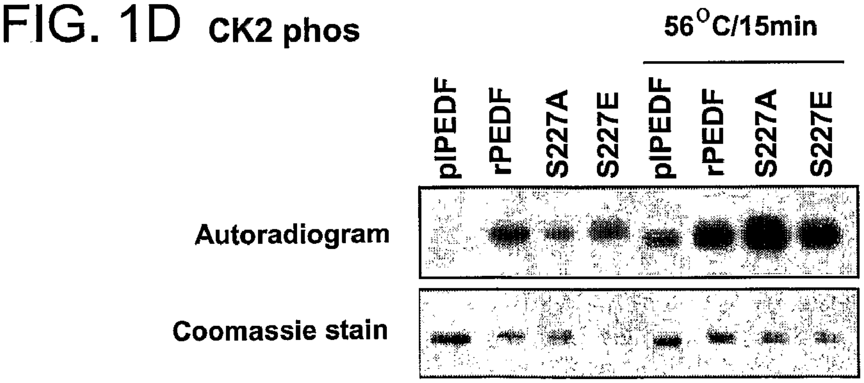

FIG. 2A
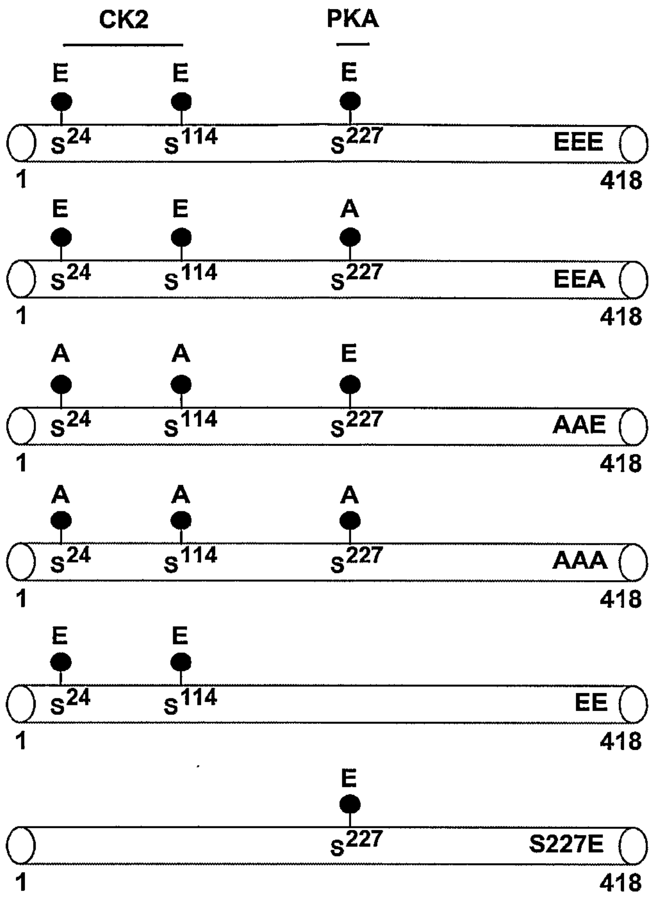
FIG. 2B CK2 phos
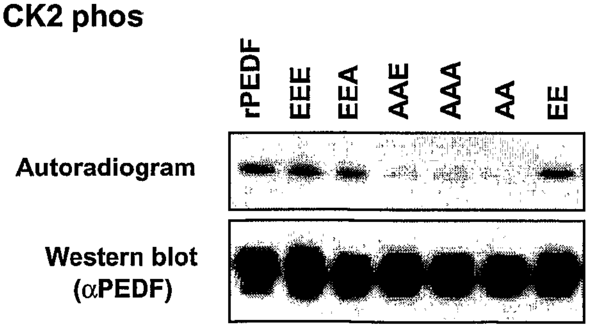
FIG. 2C PKA phos
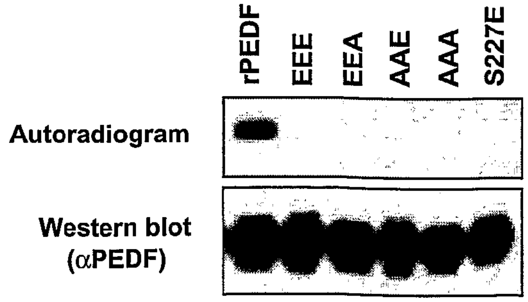

SEQUENCE LISTING

```
<160> NUMBER OF SEQ ID NOS: 17

<210> SEQ ID NO 1
<211> LENGTH: 418
<212> TYPE: PRT
<213> ORGANISM: Homo sapiens

<400> SEQUENCE: 1

Met Gln Ala Leu Val Leu Leu Leu Cys Ile Gly Ala Leu Leu Gly His
1               5                   10                  15

Ser Ser Cys Gln Asn Pro Ala Ser Pro Pro Glu Glu Gly Ser Pro Asp
            20                  25                  30

Pro Asp Ser Thr Gly Ala Leu Val Glu Glu Glu Asp Pro Phe Phe Lys
        35                  40                  45
```

-continued

```
Val Pro Val Asn Lys Leu Ala Ala Ala Val Ser Asn Phe Gly Tyr Asp
    50                  55                  60

Leu Tyr Arg Val Arg Ser Ser Met Ser Pro Thr Thr Asn Val Leu Leu
65                  70                  75                  80

Ser Pro Leu Ser Val Ala Thr Ala Leu Ser Ala Leu Ser Leu Gly Ala
                85                  90                  95

Asp Glu Arg Thr Glu Ser Ile Ile His Arg Ala Leu Tyr Tyr Asp Leu
            100                 105                 110

Ile Ser Ser Pro Asp Ile His Gly Thr Tyr Lys Glu Leu Leu Asp Thr
        115                 120                 125

Val Thr Ala Pro Gln Lys Asn Leu Lys Ser Ala Ser Arg Ile Val Phe
    130                 135                 140

Glu Lys Lys Leu Arg Ile Lys Ser Ser Phe Val Ala Pro Leu Glu Lys
145                 150                 155                 160

Ser Tyr Gly Thr Arg Pro Arg Val Leu Thr Gly Asn Pro Arg Leu Asp
                165                 170                 175

Leu Gln Glu Ile Asn Asn Trp Val Gln Ala Gln Met Lys Gly Lys Leu
            180                 185                 190

Ala Arg Ser Thr Lys Glu Ile Pro Asp Glu Ile Ser Ile Leu Leu Leu
        195                 200                 205

Gly Val Ala His Phe Lys Gly Gln Trp Val Thr Lys Phe Asp Ser Arg
    210                 215                 220

Lys Thr Ser Leu Glu Asp Phe Tyr Leu Asp Glu Glu Arg Thr Val Arg
225                 230                 235                 240

Val Pro Met Met Ser Asp Pro Lys Val Ala Leu Arg Tyr Gly Leu Asp
                245                 250                 255

Ser Asp Leu Ser Cys Lys Ile Ala Gln Leu Pro Leu Thr Gly Ser Met
            260                 265                 270

Ser Ile Ile Phe Phe Leu Pro Leu Lys Val Thr Gln Asn Leu Thr Leu
        275                 280                 285

Ile Glu Glu Ser Leu Thr Ser Glu Phe Ile His Asp Ile Asp Arg Glu
    290                 295                 300

Leu Lys Thr Val Gln Ala Val Leu Thr Val Pro Lys Leu Lys Leu Ser
305                 310                 315                 320

Tyr Glu Gly Glu Val Thr Lys Ser Leu Gln Glu Met Lys Leu Gln Ser
                325                 330                 335

Leu Phe Asp Ser Pro Asp Phe Ser Lys Ile Thr Gly Lys Pro Ile Lys
            340                 345                 350

Leu Thr Gln Val Glu His Arg Ala Gly Phe Glu Trp Asn Glu Asp Gly
        355                 360                 365

Ala Gly Thr Thr Pro Ser Pro Gly Leu Gln Pro Ala His Leu Thr Phe
    370                 375                 380

Pro Leu Asp Tyr His Leu Asn Gln Pro Phe Ile Phe Val Leu Arg Asp
385                 390                 395                 400

Thr Asp Thr Gly Ala Leu Leu Phe Ile Gly Lys Ile Leu Asp Pro Arg
                405                 410                 415

Gly Pro
```

<210> SEQ ID NO 2
<211> LENGTH: 418
<212> TYPE: PRT
<213> ORGANISM: Artificial Sequence
<220> FEATURE:
<223> OTHER INFORMATION: Synthetic protein

<400> SEQUENCE: 2

```
Met Gln Ala Leu Val Leu Leu Leu Cys Ile Gly Ala Leu Leu Gly His
1               5                   10                  15

Ser Ser Cys Gln Asn Pro Ala Glu Pro Pro Glu Glu Gly Ser Pro Asp
            20                  25                  30

Pro Asp Ser Thr Gly Ala Leu Val Glu Glu Glu Asp Pro Phe Phe Lys
        35                  40                  45

Val Pro Val Asn Lys Leu Ala Ala Ala Val Ser Asn Phe Gly Tyr Asp
    50                  55                  60

Leu Tyr Arg Val Arg Ser Ser Met Ser Pro Thr Thr Asn Val Leu Leu
65                  70                  75                  80

Ser Pro Leu Ser Val Ala Thr Ala Leu Ser Ala Leu Ser Leu Gly Ala
                85                  90                  95

Asp Glu Arg Thr Glu Ser Ile Ile His Arg Ala Leu Tyr Tyr Asp Leu
            100                 105                 110

Ile Glu Ser Pro Asp Ile His Gly Thr Tyr Lys Glu Leu Leu Asp Thr
        115                 120                 125

Val Thr Ala Pro Gln Lys Asn Leu Lys Ser Ala Ser Arg Ile Val Phe
    130                 135                 140

Glu Lys Lys Leu Arg Ile Lys Ser Ser Phe Val Ala Pro Leu Glu Lys
145                 150                 155                 160

Ser Tyr Gly Thr Arg Pro Arg Val Leu Thr Gly Asn Pro Arg Leu Asp
                165                 170                 175

Leu Gln Glu Ile Asn Asn Trp Val Gln Ala Gln Met Lys Gly Lys Leu
            180                 185                 190

Ala Arg Ser Thr Lys Glu Ile Pro Asp Glu Ile Ser Ile Leu Leu Leu
        195                 200                 205

Gly Val Ala His Phe Lys Gly Gln Trp Val Thr Lys Phe Asp Ser Arg
    210                 215                 220

Lys Thr Glu Leu Glu Asp Phe Tyr Leu Asp Glu Glu Arg Thr Val Arg
225                 230                 235                 240

Val Pro Met Met Ser Asp Pro Lys Val Ala Leu Arg Tyr Gly Leu Asp
                245                 250                 255

Ser Asp Leu Ser Cys Lys Ile Ala Gln Leu Pro Leu Thr Gly Ser Met
            260                 265                 270

Ser Ile Ile Phe Phe Leu Pro Leu Lys Val Thr Gln Asn Leu Thr Leu
        275                 280                 285

Ile Glu Glu Ser Leu Thr Ser Glu Phe Ile His Asp Ile Asp Arg Glu
    290                 295                 300

Leu Lys Thr Val Gln Ala Val Leu Thr Val Pro Lys Leu Lys Leu Ser
305                 310                 315                 320

Tyr Glu Gly Glu Val Thr Lys Ser Leu Gln Glu Met Lys Leu Gln Ser
                325                 330                 335

Leu Phe Asp Ser Pro Asp Phe Ser Lys Ile Thr Gly Lys Pro Ile Lys
            340                 345                 350

Leu Thr Gln Val Glu His Arg Ala Gly Phe Glu Trp Asn Glu Asp Gly
        355                 360                 365

Ala Gly Thr Thr Pro Ser Pro Gly Leu Gln Pro Ala His Leu Thr Phe
    370                 375                 380

Pro Leu Asp Tyr His Leu Asn Gln Pro Phe Ile Phe Val Leu Arg Asp
385                 390                 395                 400

Thr Asp Thr Gly Ala Leu Leu Phe Ile Gly Lys Ile Leu Asp Pro Arg
                405                 410                 415

Gly Pro
```

<210> SEQ ID NO 3
<211> LENGTH: 418
<212> TYPE: PRT
<213> ORGANISM: Artificial Sequence
<220> FEATURE:
<223> OTHER INFORMATION: Synthetic protein

<400> SEQUENCE: 3

Met Gln Ala Leu Val Leu Leu Leu Cys Ile Gly Ala Leu Leu Gly His
1 5 10 15

Ser Ser Cys Gln Asn Pro Ala Ala Pro Pro Glu Glu Gly Ser Pro Asp
20 25 30

Pro Asp Ser Thr Gly Ala Leu Val Glu Glu Glu Asp Pro Phe Phe Lys
35 40 45

Val Pro Val Asn Lys Leu Ala Ala Ala Val Ser Asn Phe Gly Tyr Asp
50 55 60

Leu Tyr Arg Val Arg Ser Ser Met Ser Pro Thr Thr Asn Val Leu Leu
65 70 75 80

Ser Pro Leu Ser Val Ala Thr Ala Leu Ser Ala Leu Ser Leu Gly Ala
85 90 95

Asp Glu Arg Thr Glu Ser Ile Ile His Arg Ala Leu Tyr Tyr Asp Leu
100 105 110

Ile Ala Ser Pro Asp Ile His Gly Thr Tyr Lys Glu Leu Leu Asp Thr
115 120 125

Val Thr Ala Pro Gln Lys Asn Leu Lys Ser Ala Ser Arg Ile Val Phe
130 135 140

Glu Lys Lys Leu Arg Ile Lys Ser Ser Phe Val Ala Pro Leu Glu Lys
145 150 155 160

Ser Tyr Gly Thr Arg Pro Arg Val Leu Thr Gly Asn Pro Arg Leu Asp
165 170 175

Leu Gln Glu Ile Asn Asn Trp Val Gln Ala Gln Met Lys Gly Lys Leu
180 185 190

Ala Arg Ser Thr Lys Glu Ile Pro Asp Glu Ile Ser Ile Leu Leu Leu
195 200 205

Gly Val Ala His Phe Lys Gly Gln Trp Val Thr Lys Phe Asp Ser Arg
210 215 220

Lys Thr Glu Leu Glu Asp Phe Tyr Leu Asp Glu Glu Arg Thr Val Arg
225 230 235 240

Val Pro Met Met Ser Asp Pro Lys Val Ala Leu Arg Tyr Gly Leu Asp
245 250 255

Ser Asp Leu Ser Cys Lys Ile Ala Gln Leu Pro Leu Thr Gly Ser Met
260 265 270

Ser Ile Ile Phe Phe Leu Pro Leu Lys Val Thr Gln Asn Leu Thr Leu
275 280 285

Ile Glu Glu Ser Leu Thr Ser Glu Phe Ile His Asp Ile Asp Arg Glu
290 295 300

Leu Lys Thr Val Gln Ala Val Leu Thr Val Pro Lys Leu Lys Leu Ser
305 310 315 320

Tyr Glu Gly Glu Val Thr Lys Ser Leu Gln Glu Met Lys Leu Gln Ser
325 330 335

Leu Phe Asp Ser Pro Asp Phe Ser Lys Ile Thr Gly Lys Pro Ile Lys
340 345 350

Leu Thr Gln Val Glu His Arg Ala Gly Phe Glu Trp Asn Glu Asp Gly
355 360 365

```
Ala Gly Thr Thr Pro Ser Pro Gly Leu Gln Pro Ala His Leu Thr Phe
    370                 375                 380

Pro Leu Asp Tyr His Leu Asn Gln Pro Phe Ile Phe Val Leu Arg Asp
385                 390                 395                 400

Thr Asp Thr Gly Ala Leu Leu Phe Ile Gly Lys Ile Leu Asp Pro Arg
                405                 410                 415

Gly Pro


<210> SEQ ID NO 4
<211> LENGTH: 418
<212> TYPE: PRT
<213> ORGANISM: Artificial Sequence
<220> FEATURE:
<223> OTHER INFORMATION: Synthetic protein

<400> SEQUENCE: 4

Met Gln Ala Leu Val Leu Leu Leu Cys Ile Gly Ala Leu Leu Gly His
1               5                   10                  15

Ser Ser Cys Gln Asn Pro Ala Ala Pro Pro Glu Glu Gly Ser Pro Asp
            20                  25                  30

Pro Asp Ser Thr Gly Ala Leu Val Glu Glu Glu Asp Pro Phe Phe Lys
        35                  40                  45

Val Pro Val Asn Lys Leu Ala Ala Ala Val Ser Asn Phe Gly Tyr Asp
    50                  55                  60

Leu Tyr Arg Val Arg Ser Ser Met Ser Pro Thr Thr Asn Val Leu Leu
65                  70                  75                  80

Ser Pro Leu Ser Val Ala Thr Ala Leu Ser Ala Leu Ser Leu Gly Ala
                85                  90                  95

Asp Glu Arg Thr Glu Ser Ile Ile His Arg Ala Leu Tyr Tyr Asp Leu
            100                 105                 110

Ile Ala Ser Pro Asp Ile His Gly Thr Tyr Lys Glu Leu Leu Asp Thr
        115                 120                 125

Val Thr Ala Pro Gln Lys Asn Leu Lys Ser Ala Ser Arg Ile Val Phe
    130                 135                 140

Glu Lys Lys Leu Arg Ile Lys Ser Ser Phe Val Ala Pro Leu Glu Lys
145                 150                 155                 160

Ser Tyr Gly Thr Arg Pro Arg Val Leu Thr Gly Asn Pro Arg Leu Asp
                165                 170                 175

Leu Gln Glu Ile Asn Asn Trp Val Gln Ala Gln Met Lys Gly Lys Leu
            180                 185                 190

Ala Arg Ser Thr Lys Glu Ile Pro Asp Glu Ile Ser Ile Leu Leu Leu
        195                 200                 205

Gly Val Ala His Phe Lys Gly Gln Trp Val Thr Lys Phe Asp Ser Arg
    210                 215                 220

Lys Thr Ala Leu Glu Asp Phe Tyr Leu Asp Glu Glu Arg Thr Val Arg
225                 230                 235                 240

Val Pro Met Met Ser Asp Pro Lys Val Ala Leu Arg Tyr Gly Leu Asp
                245                 250                 255

Ser Asp Leu Ser Cys Lys Ile Ala Gln Leu Pro Leu Thr Gly Ser Met
            260                 265                 270

Ser Ile Ile Phe Phe Leu Pro Leu Lys Val Thr Gln Asn Leu Thr Leu
        275                 280                 285

Ile Glu Glu Ser Leu Thr Ser Glu Phe Ile His Asp Ile Asp Arg Glu
    290                 295                 300

Leu Lys Thr Val Gln Ala Val Leu Thr Val Pro Lys Leu Lys Leu Ser
305                 310                 315                 320
```

```
Tyr Glu Gly Glu Val Thr Lys Ser Leu Gln Glu Met Lys Leu Gln Ser
                325                 330                 335

Leu Phe Asp Ser Pro Asp Phe Ser Lys Ile Thr Gly Lys Pro Ile Lys
            340                 345                 350

Leu Thr Gln Val Glu His Arg Ala Gly Phe Glu Trp Asn Glu Asp Gly
        355                 360                 365

Ala Gly Thr Thr Pro Ser Pro Gly Leu Gln Pro Ala His Leu Thr Phe
    370                 375                 380

Pro Leu Asp Tyr His Leu Asn Gln Pro Phe Ile Phe Val Leu Arg Asp
385                 390                 395                 400

Thr Asp Thr Gly Ala Leu Leu Phe Ile Gly Lys Ile Leu Asp Pro Arg
                405                 410                 415

Gly Pro


<210> SEQ ID NO 5
<211> LENGTH: 418
<212> TYPE: PRT
<213> ORGANISM: Artificial Sequence
<220> FEATURE:
<223> OTHER INFORMATION: Synthetic protein

<400> SEQUENCE: 5

Met Gln Ala Leu Val Leu Leu Leu Cys Ile Gly Ala Leu Leu Gly His
1               5                   10                  15

Ser Ser Cys Gln Asn Pro Ala Glu Pro Pro Glu Glu Gly Ser Pro Asp
            20                  25                  30

Pro Asp Ser Thr Gly Ala Leu Val Glu Glu Glu Asp Pro Phe Phe Lys
        35                  40                  45

Val Pro Val Asn Lys Leu Ala Ala Ala Val Ser Asn Phe Gly Tyr Asp
    50                  55                  60

Leu Tyr Arg Val Arg Ser Ser Met Ser Pro Thr Thr Asn Val Leu Leu
65                  70                  75                  80

Ser Pro Leu Ser Val Ala Thr Ala Leu Ser Ala Leu Ser Leu Gly Ala
                85                  90                  95

Asp Glu Arg Thr Glu Ser Ile Ile His Arg Ala Leu Tyr Tyr Asp Leu
            100                 105                 110

Ile Glu Ser Pro Asp Ile His Gly Thr Tyr Lys Glu Leu Leu Asp Thr
        115                 120                 125

Val Thr Ala Pro Gln Lys Asn Leu Lys Ser Ala Ser Arg Ile Val Phe
    130                 135                 140

Glu Lys Lys Leu Arg Ile Lys Ser Ser Phe Val Ala Pro Leu Glu Lys
145                 150                 155                 160

Ser Tyr Gly Thr Arg Pro Arg Val Leu Thr Gly Asn Pro Arg Leu Asp
                165                 170                 175

Leu Gln Glu Ile Asn Asn Trp Val Gln Ala Gln Met Lys Gly Lys Leu
            180                 185                 190

Ala Arg Ser Thr Lys Glu Ile Pro Asp Glu Ile Ser Ile Leu Leu Leu
        195                 200                 205

Gly Val Ala His Phe Lys Gly Gln Trp Val Thr Lys Phe Asp Ser Arg
    210                 215                 220

Lys Thr Ala Leu Glu Asp Phe Tyr Leu Asp Glu Glu Arg Thr Val Arg
225                 230                 235                 240

Val Pro Met Met Ser Asp Pro Lys Val Ala Leu Arg Tyr Gly Leu Asp
                245                 250                 255

Ser Asp Leu Ser Cys Lys Ile Ala Gln Leu Pro Leu Thr Gly Ser Met
```

-continued

```
            260                 265                 270

Ser Ile Ile Phe Phe Leu Pro Leu Lys Val Thr Gln Asn Leu Thr Leu
        275                 280                 285

Ile Glu Glu Ser Leu Thr Ser Glu Phe Ile His Asp Ile Asp Arg Glu
    290                 295                 300

Leu Lys Thr Val Gln Ala Val Leu Thr Val Pro Lys Leu Lys Leu Ser
305                 310                 315                 320

Tyr Glu Gly Glu Val Thr Lys Ser Leu Gln Glu Met Lys Leu Gln Ser
                325                 330                 335

Leu Phe Asp Ser Pro Asp Phe Ser Lys Ile Thr Gly Lys Pro Ile Lys
            340                 345                 350

Leu Thr Gln Val Glu His Arg Ala Gly Phe Glu Trp Asn Glu Asp Gly
        355                 360                 365

Ala Gly Thr Thr Pro Ser Pro Gly Leu Gln Pro Ala His Leu Thr Phe
    370                 375                 380

Pro Leu Asp Tyr His Leu Asn Gln Pro Phe Ile Phe Val Leu Arg Asp
385                 390                 395                 400

Thr Asp Thr Gly Ala Leu Leu Phe Ile Gly Lys Ile Leu Asp Pro Arg
                405                 410                 415

Gly Pro
```

<210> SEQ ID NO 6
<211> LENGTH: 1257
<212> TYPE: DNA
<213> ORGANISM: Homo sapiens

<400> SEQUENCE: 6

```
atgcaggccc tggtgctact cctctgcatt ggagccctcc tcgggcacag cagctgccag     60

aaccctgcca gcccccccgga ggaaggctcc ccagaccccg acagcacagg ggcgctggtg    120

gaggaggagg atcctttctt caaagtcccc gtgaacaagc tggcagcggc tgtctccaac    180

ttcggctatg acctgtaccg ggtgcgatcc agcatgagcc ccacgaccaa cgtgctcctg    240

tctcctctca gtgtggccac ggccctctcg gccctctcgc tgggagcgga gcagcgaaca    300

gaatccatca ttcaccgggc tctctactat gacttgatca gcagcccaga catccatggt    360

acctataagg agctccttga cacggtcact gccccccaga agaacctcaa gagtgcctcc    420

cggatcgtct ttgagaagaa gctgcgcata aaatccagct ttgtggcacc tctggaaaag    480

tcatatggga ccaggcccag agtcctgacg ggcaaccctc gcttggacct gcaagagatc    540

aacaactggg tgcaggcgca gatgaaaggg aagctcgcca ggtccacaaa ggaaattccc    600

gatgagatca gcattctcct tctcggtgtg gcgcacttca aggggcagtg ggtaacaaag    660

tttgactcca gaaagacttc cctcgaggat ttctacttgg atgaagagag gaccgtgagg    720

gtccccatga tgtcggaccc taaggctgtt ttacgctatg gcttggattc agatctcagc    780

tgcaagattg cccagctgcc cttgaccgga agcatgagta tcatcttctt cctgcccctg    840

aaagtgaccc agaatttgac cttgatagag gagagcctca cctccgagtt cattcatgac    900

atagaccgag aactgaagac cgtgcaggcg gtcctcactg tccccaagct gaagctgagt    960

tacgaaggcg aagtcaccaa gtccctgcag gagatgaagc tgcaatcctt gtttgattca   1020

ccagacttta gcaagatcac aggcaaaccc atcaagctga ctcaggtgga acaccgggct   1080

ggctttgagt ggaacgagga tggggcggga accacccccca gcccagggct gcagcctgcc   1140

cacctcacct tcccgctgga ctatcacctt aaccagcctt tcatcttcgt actgagggac   1200

acagacacag ggcccttct cttcattggc aagattctgg accccagggg cccctaa      1257
```

<210> SEQ ID NO 7
<211> LENGTH: 1257
<212> TYPE: DNA
<213> ORGANISM: Artificial Sequence
<220> FEATURE:
<223> OTHER INFORMATION: Synthetic cDNA
<220> FEATURE:
<221> NAME/KEY: misc_feature
<222> LOCATION: (72)..(72)
<223> OTHER INFORMATION: n= G or A
<220> FEATURE:
<221> NAME/KEY: misc_feature
<222> LOCATION: (342)..(342)
<223> OTHER INFORMATION: n= A or G
<220> FEATURE:
<221> NAME/KEY: misc_feature
<222> LOCATION: (681)..(681)
<223> OTHER INFORMATION: n= A or G

<400> SEQUENCE: 7
atgcaggccc tggtgctact cctctgcatt ggagccctcc tcgggcacag cagctgccag 60
aaccctgccg anccccgga ggaaggctcc ccagaccccg acagcacagg ggcgctggtg 120
gaggaggagg atcctttctt caaagtcccc gtgaacaagc tggcagcggc tgtctccaac 180
ttcggctatg acctgtaccg ggtgcgatcc agcatgagcc ccacgaccaa cgtgctcctg 240
tctcctctca gtgtggccac ggccctctcg gccctctcgc tgggagcgga gcagcgaaca 300
gaatccatca ttcaccgggc tctctactat gacttgatcg anagcccaga catccatggt 360
acctataagg agctccttga cacggtcact gccccccaga agaacctcaa gagtgcctcc 420
cggatcgtct ttgagaagaa gctgcgcata aaatccagct ttgtggcacc tctggaaaag 480
tcatatggga ccaggcccag agtcctgacg ggcaaccctc gcttggacct gcaagagatc 540
aacaactggg tgcaggcgca gatgaaaggg aagctcgcca ggtccacaaa ggaaattccc 600
gatgagatca gcattctcct tctcggtgtg gcgcacttca aggggcagtg ggtaacaaag 660
tttgactcca gaaagactga nctcgaggat ttctacttgg atgaagagag gaccgtgagg 720
gtccccatga tgtcggaccc taaggctgtt ttacgctatg gcttggattc agatctcagc 780
tgcaagattg cccagctgcc cttgaccgga agcatgagta tcatcttctt cctgcccctg 840
aaagtgaccc agaatttgac cttgatagag gagagcctca cctccgagtt cattcatgac 900
atagaccgag aactgaagac cgtgcaggcg gtcctcactg tccccaagct gaagctgagt 960
tacgaaggcg aagtcaccaa gtccctgcag gagatgaagc tgcaatcctt gtttgattca 1020
ccagacttta gcaagatcac aggcaaaccc atcaagctga ctcaggtgga acaccgggct 1080
ggctttgagt ggaacgagga tggggcggga accaccccca gcccagggct gcagcctgcc 1140
cacctcacct tcccgctgga ctatcacctt aaccagcctt tcatcttcgt actgagggac 1200
acagacacag ggcccttct cttcattggc aagattctgg accccagggg cccctaa 1257

<210> SEQ ID NO 8
<211> LENGTH: 1257
<212> TYPE: DNA
<213> ORGANISM: Artificial Sequence
<220> FEATURE:
<223> OTHER INFORMATION: Synthetic cDNA
<220> FEATURE:
<221> NAME/KEY: misc_feature
<222> LOCATION: (72)..(72)
<223> OTHER INFORMATION: n= C, A, G or T
<220> FEATURE:
<221> NAME/KEY: misc_feature
<222> LOCATION: (342)..(342)
<223> OTHER INFORMATION: n= C, A, G or T
<220> FEATURE:
<221> NAME/KEY: misc_feature
<222> LOCATION: (681)..(681)
<223> OTHER INFORMATION: n= A or G

<400> SEQUENCE: 8

```
atgcaggccc tggtgctact cctctgcatt ggagccctcc tcgggcacag cagctgccag      60

aaccctgccg cncccccgga ggaaggctcc ccagaccccg acagcacagg ggcgctggtg     120

gaggaggagg atcctttctt caaagtcccc gtgaacaagc tggcagcggc tgtctccaac     180

ttcggctatg acctgtaccg ggtgcgatcc agcatgagcc ccacgaccaa cgtgctcctg     240

tctcctctca gtgtggccac ggccctctcg gccctctcgc tgggagcgga gcagcgaaca     300

gaatccatca ttcaccgggc tctctactat gacttgatcg cnagcccaga catccatggt     360

acctataagg agctccttga cacggtcact gccccccaga agaacctcaa gagtgcctcc     420

cggatcgtct ttgagaagaa gctgcgcata aaatccagct ttgtggcacc tctggaaaag     480

tcatatggga ccaggcccag agtcctgacg ggcaaccctc gcttggacct gcaagagatc     540

aacaactggg tgcaggcgca gatgaaaggg aagctcgcca ggtccacaaa ggaaattccc     600

gatgagatca gcattctcct tctcggtgtg gcgcacttca aggggcagtg ggtaacaaag     660

tttgactcca gaaagactga nctcgaggat ttctacttgg atgaagagag gaccgtgagg     720

gtccccatga tgtcggaccc taaggctgtt ttacgctatg gcttggattc agatctcagc     780

tgcaagattg cccagctgcc cttgaccgga agcatgagta tcatcttctt cctgcccctg     840

aaagtgaccc agaatttgac cttgatagag gagagcctca cctccgagtt cattcatgac     900

atagaccgag aactgaagac cgtgcaggcg gtcctcactg tccccaagct gaagctgagt     960

tacgaaggcg aagtcaccaa gtccctgcag gagatgaagc tgcaatcctt gtttgattca    1020

ccagacttta gcaagatcac aggcaaaccc atcaagctga ctcaggtgga acaccgggct    1080

ggctttgagt ggaacgagga tggggcggga accaccccca gcccagggct gcagcctgcc    1140

cacctcacct tcccgctgga ctatcacctt aaccagcctt tcatcttcgt actgagggac    1200

acagacacag ggcccttct cttcattggc aagattctgg accccagggg cccctaa        1257
```

<210> SEQ ID NO 9
<211> LENGTH: 1257
<212> TYPE: DNA
<213> ORGANISM: Artificial Sequence
<220> FEATURE:
<223> OTHER INFORMATION: Synthetic cDNA
<220> FEATURE:
<221> NAME/KEY: misc_feature
<222> LOCATION: (72)..(72)
<223> OTHER INFORMATION: n= C, A, G or T
<220> FEATURE:
<221> NAME/KEY: misc_feature
<222> LOCATION: (342)..(342)
<223> OTHER INFORMATION: n= C, A, G or T
<220> FEATURE:
<221> NAME/KEY: misc_feature
<222> LOCATION: (681)..(681)
<223> OTHER INFORMATION: n= C, A, G or T

<400> SEQUENCE: 9

```
atgcaggccc tggtgctact cctctgcatt ggagccctcc tcgggcacag cagctgccag      60

aaccctgccg cncccccgga ggaaggctcc ccagaccccg acagcacagg ggcgctggtg     120

gaggaggagg atcctttctt caaagtcccc gtgaacaagc tggcagcggc tgtctccaac     180

ttcggctatg acctgtaccg ggtgcgatcc agcatgagcc ccacgaccaa cgtgctcctg     240

tctcctctca gtgtggccac ggccctctcg gccctctcgc tgggagcgga gcagcgaaca     300
```

```
gaatccatca ttcaccgggc tctctactat gacttgatcg cnagcccaga catccatggt    360

acctataagg agctccttga cacggtcact gccccccaga agaacctcaa gagtgcctcc    420

cggatcgtct ttgagaagaa gctgcgcata aaatccagct ttgtggcacc tctggaaaag    480

tcatatggga ccaggcccag agtcctgacg ggcaaccctc gcttggacct gcaagagatc    540

aacaactggg tgcaggcgca gatgaaaggg aagctcgcca ggtccacaaa ggaaattccc    600

gatgagatca gcattctcct tctcggtgtg gcgcacttca aggggcagtg ggtaacaaag    660

tttgactcca gaaagactgc nctcgaggat ttctacttgg atgaagagag gaccgtgagg    720

gtccccatga tgtcggaccc taaggctgtt ttacgctatg gcttggattc agatctcagc    780

tgcaagattg cccagctgcc cttgaccgga agcatgagta tcatcttctt cctgcccctg    840

aaagtgaccc agaatttgac cttgatagag gagagcctca cctccgagtt cattcatgac    900

atagaccgag aactgaagac cgtgcaggcg gtcctcactg tccccaagct gaagctgagt    960

tacgaaggcg aagtcaccaa gtccctgcag gagatgaagc tgcaatcctt gtttgattca   1020

ccagacttta gcaagatcac aggcaaaccc atcaagctga ctcaggtgga acaccgggct   1080

ggctttgagt ggaacgagga tggggcggga accacccccca gcccagggct gcagcctgcc  1140

cacctcacct tcccgctgga ctatcacctt aaccagcctt tcatcttcgt actgagggac   1200

acagacacag ggcccttct cttcattggc aagattctgg accccagggg cccctaa       1257
```

<210> SEQ ID NO 10
<211> LENGTH: 1257
<212> TYPE: DNA
<213> ORGANISM: Artificial Sequence
<220> FEATURE:
<223> OTHER INFORMATION: Synthetic cDNA
<220> FEATURE:
<221> NAME/KEY: misc_feature
<222> LOCATION: (72)..(72)
<223> OTHER INFORMATION: n= G or A
<220> FEATURE:
<221> NAME/KEY: misc_feature
<222> LOCATION: (342)..(342)
<223> OTHER INFORMATION: n= A or G
<220> FEATURE:
<221> NAME/KEY: misc_feature
<222> LOCATION: (681)..(681)
<223> OTHER INFORMATION: n= C, A, G or T

<400> SEQUENCE: 10

```
atgcaggccc tggtgctact cctctgcatt ggagccctcc tcgggcacag cagctgccag     60

aaccctgccg anccccgga ggaaggctcc ccagaccccg acagcacagg ggcgctggtg    120

gaggaggagg atcctttctt caaagtcccc gtgaacaagc tggcagcggc tgtctccaac    180

ttcggctatg acctgtaccg ggtgcgatcc agcatgagcc ccacgaccaa cgtgctcctg    240

tctcctctca gtgtggccac ggccctctcg gccctctcgc tgggagcgga gcagcgaaca    300

gaatccatca ttcaccgggc tctctactat gacttgatcg anagcccaga catccatggt    360

acctataagg agctccttga cacggtcact gccccccaga agaacctcaa gagtgcctcc    420

cggatcgtct ttgagaagaa gctgcgcata aaatccagct ttgtggcacc tctggaaaag    480

tcatatggga ccaggcccag agtcctgacg ggcaaccctc gcttggacct gcaagagatc    540

aacaactggg tgcaggcgca gatgaaaggg aagctcgcca ggtccacaaa ggaaattccc    600

gatgagatca gcattctcct tctcggtgtg gcgcacttca aggggcagtg ggtaacaaag    660

tttgactcca gaaagactgc nctcgaggat ttctacttgg atgaagagag gaccgtgagg    720

gtccccatga tgtcggaccc taaggctgtt ttacgctatg gcttggattc agatctcagc    780
```

-continued

```
tgcaagattg cccagctgcc cttgaccgga agcatgagta tcatcttctt cctgcccctg    840

aaagtgaccc agaatttgac cttgatagag gagagcctca cctccgagtt cattcatgac    900

atagaccgag aactgaagac cgtgcaggcg gtcctcactg tccccaagct gaagctgagt    960

tacgaaggcg aagtcaccaa gtccctgcag gagatgaagc tgcaatcctt gtttgattca   1020

ccagacttta gcaagatcac aggcaaaccc atcaagctga ctcaggtgga acaccgggct   1080

ggctttgagt ggaacgagga tggggcggga accacccccca gcccagggct gcagcctgcc  1140

cacctcacct tcccgctgga ctatcacctt aaccagcctt tcatcttcgt actgagggac   1200

acagacacag ggcccttct cttcattggc aagattctgg accccagggg cccctaa       1257
```

```
<210> SEQ ID NO 11
<211> LENGTH: 418
<212> TYPE: PRT
<213> ORGANISM: Artificial Sequence
<220> FEATURE:
<223> OTHER INFORMATION: Synthetic protein

<400> SEQUENCE: 11

Met Gln Ala Leu Val Leu Leu Leu Cys Ile Gly Ala Leu Leu Gly His
1               5                   10                  15

Ser Ser Cys Gln Asn Pro Ala Glu Pro Pro Glu Glu Gly Ser Pro Asp
            20                  25                  30

Pro Asp Ser Thr Gly Ala Leu Val Glu Glu Glu Asp Pro Phe Phe Lys
        35                  40                  45

Val Pro Val Asn Lys Leu Ala Ala Ala Val Ser Asn Phe Gly Tyr Asp
    50                  55                  60

Leu Tyr Arg Val Arg Ser Ser Met Ser Pro Thr Thr Asn Val Leu Leu
65                  70                  75                  80

Ser Pro Leu Ser Val Ala Thr Ala Leu Ser Ala Leu Ser Leu Gly Ala
                85                  90                  95

Asp Glu Arg Thr Glu Ser Ile Ile His Arg Ala Leu Tyr Tyr Asp Leu
            100                 105                 110

Ile Ser Ser Pro Asp Ile His Gly Thr Tyr Lys Glu Leu Leu Asp Thr
        115                 120                 125

Val Thr Ala Pro Gln Lys Asn Leu Lys Ser Ala Ser Arg Ile Val Phe
    130                 135                 140

Glu Lys Lys Leu Arg Ile Lys Ser Ser Phe Val Ala Pro Leu Glu Lys
145                 150                 155                 160

Ser Tyr Gly Thr Arg Pro Arg Val Leu Thr Gly Asn Pro Arg Leu Asp
                165                 170                 175

Leu Gln Glu Ile Asn Asn Trp Val Gln Ala Gln Met Lys Gly Lys Leu
            180                 185                 190

Ala Arg Ser Thr Lys Glu Ile Pro Asp Glu Ile Ser Ile Leu Leu Leu
        195                 200                 205

Gly Val Ala His Phe Lys Gly Gln Trp Val Thr Lys Phe Asp Ser Arg
    210                 215                 220

Lys Thr Ser Leu Glu Asp Phe Tyr Leu Asp Glu Glu Arg Thr Val Arg
225                 230                 235                 240

Val Pro Met Met Ser Asp Pro Lys Val Ala Leu Arg Tyr Gly Leu Asp
                245                 250                 255

Ser Asp Leu Ser Cys Lys Ile Ala Gln Leu Pro Leu Thr Gly Ser Met
            260                 265                 270

Ser Ile Ile Phe Phe Leu Pro Leu Lys Val Thr Gln Asn Leu Thr Leu
        275                 280                 285
```

Ile Glu Glu Ser Leu Thr Ser Glu Phe Ile His Asp Ile Asp Arg Glu
290 295 300

Leu Lys Thr Val Gln Ala Val Leu Thr Val Pro Lys Leu Lys Leu Ser
305 310 315 320

Tyr Glu Gly Glu Val Thr Lys Ser Leu Gln Glu Met Lys Leu Gln Ser
325 330 335

Leu Phe Asp Ser Pro Asp Phe Ser Lys Ile Thr Gly Lys Pro Ile Lys
340 345 350

Leu Thr Gln Val Glu His Arg Ala Gly Phe Glu Trp Asn Glu Asp Gly
355 360 365

Ala Gly Thr Thr Pro Ser Pro Gly Leu Gln Pro Ala His Leu Thr Phe
370 375 380

Pro Leu Asp Tyr His Leu Asn Gln Pro Phe Ile Phe Val Leu Arg Asp
385 390 395 400

Thr Asp Thr Gly Ala Leu Leu Phe Ile Gly Lys Ile Leu Asp Pro Arg
405 410 415

Gly Pro

<210> SEQ ID NO 12
<211> LENGTH: 418
<212> TYPE: PRT
<213> ORGANISM: Artificial Sequence
<220> FEATURE:
<223> OTHER INFORMATION: Synthetic protein

<400> SEQUENCE: 12

Met Gln Ala Leu Val Leu Leu Leu Cys Ile Gly Ala Leu Leu Gly His
1 5 10 15

Ser Ser Cys Gln Asn Pro Ala Glu Pro Pro Glu Glu Gly Ser Pro Asp
20 25 30

Pro Asp Ser Thr Gly Ala Leu Val Glu Glu Glu Asp Pro Phe Phe Lys
35 40 45

Val Pro Val Asn Lys Leu Ala Ala Ala Val Ser Asn Phe Gly Tyr Asp
50 55 60

Leu Tyr Arg Val Arg Ser Ser Met Ser Pro Thr Thr Asn Val Leu Leu
65 70 75 80

Ser Pro Leu Ser Val Ala Thr Ala Leu Ser Ala Leu Ser Leu Gly Ala
85 90 95

Asp Glu Arg Thr Glu Ser Ile Ile His Arg Ala Leu Tyr Tyr Asp Leu
100 105 110

Ile Glu Ser Pro Asp Ile His Gly Thr Tyr Lys Glu Leu Leu Asp Thr
115 120 125

Val Thr Ala Pro Gln Lys Asn Leu Lys Ser Ala Ser Arg Ile Val Phe
130 135 140

Glu Lys Lys Leu Arg Ile Lys Ser Ser Phe Val Ala Pro Leu Glu Lys
145 150 155 160

Ser Tyr Gly Thr Arg Pro Arg Val Leu Thr Gly Asn Pro Arg Leu Asp
165 170 175

Leu Gln Glu Ile Asn Asn Trp Val Gln Ala Gln Met Lys Gly Lys Leu
180 185 190

Ala Arg Ser Thr Lys Glu Ile Pro Asp Glu Ile Ser Ile Leu Leu Leu
195 200 205

Gly Val Ala His Phe Lys Gly Gln Trp Val Thr Lys Phe Asp Ser Arg
210 215 220

Lys Thr Ser Leu Glu Asp Phe Tyr Leu Asp Glu Glu Arg Thr Val Arg

-continued 225 230 235 240

Val Pro Met Met Ser Asp Pro Lys Val Ala Leu Arg Tyr Gly Leu Asp
245 250 255

Ser Asp Leu Ser Cys Lys Ile Ala Gln Leu Pro Leu Thr Gly Ser Met
260 265 270

Ser Ile Ile Phe Phe Leu Pro Leu Lys Val Thr Gln Asn Leu Thr Leu
275 280 285

Ile Glu Glu Ser Leu Thr Ser Glu Phe Ile His Asp Ile Asp Arg Glu
290 295 300

Leu Lys Thr Val Gln Ala Val Leu Thr Val Pro Lys Leu Lys Leu Ser
305 310 315 320

Tyr Glu Gly Glu Val Thr Lys Ser Leu Gln Glu Met Lys Leu Gln Ser
325 330 335

Leu Phe Asp Ser Pro Asp Phe Ser Lys Ile Thr Gly Lys Pro Ile Lys
340 345 350

Leu Thr Gln Val Glu His Arg Ala Gly Phe Glu Trp Asn Glu Asp Gly
355 360 365

Ala Gly Thr Thr Pro Ser Pro Gly Leu Gln Pro Ala His Leu Thr Phe
370 375 380

Pro Leu Asp Tyr His Leu Asn Gln Pro Phe Ile Phe Val Leu Arg Asp
385 390 395 400

Thr Asp Thr Gly Ala Leu Leu Phe Ile Gly Lys Ile Leu Asp Pro Arg
405 410 415

Gly Pro

<210> SEQ ID NO 13
<211> LENGTH: 418
<212> TYPE: PRT
<213> ORGANISM: Artificial Sequence
<220> FEATURE:
<223> OTHER INFORMATION: Synthetic protein

<400> SEQUENCE: 13

Met Gln Ala Leu Val Leu Leu Leu Cys Ile Gly Ala Leu Leu Gly His
1 5 10 15

Ser Ser Cys Gln Asn Pro Ala Ser Pro Pro Glu Glu Gly Ser Pro Asp
20 25 30

Pro Asp Ser Thr Gly Ala Leu Val Glu Glu Glu Asp Pro Phe Phe Lys
35 40 45

Val Pro Val Asn Lys Leu Ala Ala Ala Val Ser Asn Phe Gly Tyr Asp
50 55 60

Leu Tyr Arg Val Arg Ser Ser Met Ser Pro Thr Thr Asn Val Leu Leu
65 70 75 80

Ser Pro Leu Ser Val Ala Thr Ala Leu Ser Ala Leu Ser Leu Gly Ala
85 90 95

Asp Glu Arg Thr Glu Ser Ile Ile His Arg Ala Leu Tyr Tyr Asp Leu
100 105 110

Ile Ser Ser Pro Asp Ile His Gly Thr Tyr Lys Glu Leu Leu Asp Thr
115 120 125

Val Thr Ala Pro Gln Lys Asn Leu Lys Ser Ala Ser Arg Ile Val Phe
130 135 140

Glu Lys Lys Leu Arg Ile Lys Ser Ser Phe Val Ala Pro Leu Glu Lys
145 150 155 160

Ser Tyr Gly Thr Arg Pro Arg Val Leu Thr Gly Asn Pro Arg Leu Asp
165 170 175

Leu Gln Glu Ile Asn Asn Trp Val Gln Ala Gln Met Lys Gly Lys Leu
180 185 190

Ala Arg Ser Thr Lys Glu Ile Pro Asp Glu Ile Ser Ile Leu Leu Leu
195 200 205

Gly Val Ala His Phe Lys Gly Gln Trp Val Thr Lys Phe Asp Ser Arg
210 215 220

Lys Thr Glu Leu Glu Asp Phe Tyr Leu Asp Glu Glu Arg Thr Val Arg
225 230 235 240

Val Pro Met Met Ser Asp Pro Lys Val Ala Leu Arg Tyr Gly Leu Asp
245 250 255

Ser Asp Leu Ser Cys Lys Ile Ala Gln Leu Pro Leu Thr Gly Ser Met
260 265 270

Ser Ile Ile Phe Phe Leu Pro Leu Lys Val Thr Gln Asn Leu Thr Leu
275 280 285

Ile Glu Glu Ser Leu Thr Ser Glu Phe Ile His Asp Ile Asp Arg Glu
290 295 300

Leu Lys Thr Val Gln Ala Val Leu Thr Val Pro Lys Leu Lys Leu Ser
305 310 315 320

Tyr Glu Gly Glu Val Thr Lys Ser Leu Gln Glu Met Lys Leu Gln Ser
325 330 335

Leu Phe Asp Ser Pro Asp Phe Ser Lys Ile Thr Gly Lys Pro Ile Lys
340 345 350

Leu Thr Gln Val Glu His Arg Ala Gly Phe Glu Trp Asn Glu Asp Gly
355 360 365

Ala Gly Thr Thr Pro Ser Pro Gly Leu Gln Pro Ala His Leu Thr Phe
370 375 380

Pro Leu Asp Tyr His Leu Asn Gln Pro Phe Ile Phe Val Leu Arg Asp
385 390 395 400

Thr Asp Thr Gly Ala Leu Leu Phe Ile Gly Lys Ile Leu Asp Pro Arg
405 410 415

Gly Pro

<210> SEQ ID NO 14
<211> LENGTH: 418
<212> TYPE: PRT
<213> ORGANISM: Artificial Sequence
<220> FEATURE:
<223> OTHER INFORMATION: Synthetic protein

<400> SEQUENCE: 14

Met Gln Ala Leu Val Leu Leu Leu Cys Ile Gly Ala Leu Leu Gly His
1 5 10 15

Ser Ser Cys Gln Asn Pro Ala Ser Pro Pro Glu Glu Gly Ser Pro Asp
20 25 30

Pro Asp Ser Thr Gly Ala Leu Val Glu Glu Glu Asp Pro Phe Phe Lys
35 40 45

Val Pro Val Asn Lys Leu Ala Ala Ala Val Ser Asn Phe Gly Tyr Asp
50 55 60

Leu Tyr Arg Val Arg Ser Ser Met Ser Pro Thr Thr Asn Val Leu Leu
65 70 75 80

Ser Pro Leu Ser Val Ala Thr Ala Leu Ser Ala Leu Ser Leu Gly Ala
85 90 95

Asp Glu Arg Thr Glu Ser Ile Ile His Arg Ala Leu Tyr Tyr Asp Leu
100 105 110

Ile Glu Ser Pro Asp Ile His Gly Thr Tyr Lys Glu Leu Leu Asp Thr
115 120 125

Val Thr Ala Pro Gln Lys Asn Leu Lys Ser Ala Ser Arg Ile Val Phe
    130                 135                 140

Glu Lys Lys Leu Arg Ile Lys Ser Ser Phe Val Ala Pro Leu Glu Lys
145                 150                 155                 160

Ser Tyr Gly Thr Arg Pro Arg Val Leu Thr Gly Asn Pro Arg Leu Asp
                165                 170                 175

Leu Gln Glu Ile Asn Asn Trp Val Gln Ala Gln Met Lys Gly Lys Leu
            180                 185                 190

Ala Arg Ser Thr Lys Glu Ile Pro Asp Glu Ile Ser Ile Leu Leu Leu
        195                 200                 205

Gly Val Ala His Phe Lys Gly Gln Trp Val Thr Lys Phe Asp Ser Arg
    210                 215                 220

Lys Thr Ser Leu Glu Asp Phe Tyr Leu Asp Glu Glu Arg Thr Val Arg
225                 230                 235                 240

Val Pro Met Met Ser Asp Pro Lys Val Ala Leu Arg Tyr Gly Leu Asp
                245                 250                 255

Ser Asp Leu Ser Cys Lys Ile Ala Gln Leu Pro Leu Thr Gly Ser Met
            260                 265                 270

Ser Ile Ile Phe Phe Leu Pro Leu Lys Val Thr Gln Asn Leu Thr Leu
        275                 280                 285

Ile Glu Glu Ser Leu Thr Ser Glu Phe Ile His Asp Ile Asp Arg Glu
    290                 295                 300

Leu Lys Thr Val Gln Ala Val Leu Thr Val Pro Lys Leu Lys Leu Ser
305                 310                 315                 320

Tyr Glu Gly Glu Val Thr Lys Ser Leu Gln Glu Met Lys Leu Gln Ser
                325                 330                 335

Leu Phe Asp Ser Pro Asp Phe Ser Lys Ile Thr Gly Lys Pro Ile Lys
            340                 345                 350

Leu Thr Gln Val Glu His Arg Ala Gly Phe Glu Trp Asn Glu Asp Gly
        355                 360                 365

Ala Gly Thr Thr Pro Ser Pro Gly Leu Gln Pro Ala His Leu Thr Phe
    370                 375                 380

Pro Leu Asp Tyr His Leu Asn Gln Pro Phe Ile Phe Val Leu Arg Asp
385                 390                 395                 400

Thr Asp Thr Gly Ala Leu Leu Phe Ile Gly Lys Ile Leu Asp Pro Arg
                405                 410                 415

Gly Pro

<210> SEQ ID NO 15
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (11)..(11)
<223> OTHER INFORMATION: PHOSPHORYLATION

<400> SEQUENCE: 15

Leu Gly His Ser Ser Cys Gln Asn Pro Ala Ser Pro Pro Glu Glu Gly
1               5                   10                  15

<210> SEQ ID NO 16
<211> LENGTH: 15
<212> TYPE: PRT
<213> ORGANISM: Artificial Sequence
<220> FEATURE:

-continued

```
<223> OTHER INFORMATION: Synthetic peptide
<220> FEATURE:
<221> NAME/KEY: MOD_RES
<222> LOCATION: (9)..(9)
<223> OTHER INFORMATION: PHOSPHORYLATION

<400> SEQUENCE: 16

Thr Lys Phe Asp Ser Arg Lys Thr Ser Leu Glu Asp Phe Tyr Leu
1               5                   10                  15


<210> SEQ ID NO 17
<211> LENGTH: 17
<212> TYPE: PRT
<213> ORGANISM: Artificial Sequence
<220> FEATURE:
<223> OTHER INFORMATION: Synthetic peptide

<400> SEQUENCE: 17

Lys Ser Leu Gln Glu Met Lys Leu Gln Ser Leu Phe Asp Ser Pro Asp
1               5                   10                  15

Phe
```

VARIANTS OF PIGMENT EPITHELIUM DERIVED FACTOR AND USES THEREOF

RELATED APPLICATION DATA

This application is the U.S. national stage of PCT/IL2006/001314 filed on Nov. 14, 2006, which is based on and claims the benefit of U.S. provisional application No. 60/735,875 filed on Nov. 14, 2005, the content of each of which is expressly incorporated herein in its entirety by reference hereto.

FIELD OF THE INVENTION

The present invention relates to anti-angiogenic variants of pigment epithelium derived factor (PEDF) comprising a plurality of altered phosphorylation sites, polynucleotides encoding same and uses thereof. In particular, PEDF variants comprising a plurality of altered phosphorylation sites provide superior anti-angiogenic activity and high neurotrophic activity and are useful in treating diseases associated with neovascularization and with neurodegenerative conditions.

BACKGROUND OF THE INVENTION

The pigment epithelium derived factor (PEDF) is a member of the serine protease inhibitors (serpin) superfamily, but as of today was not found to exhibit inhibitory activity against any proteases. It was first isolated based on its ability to convert dividing retinoblastoma cells into differentiated neurons, and thus was characterized as a neurotrophic factor. Later on it was shown that besides its neurotrophic functions, PEDF is a potent natural inhibitor of angiogenesis in the eye, where it inhibits stimulatory activity of several strong proangiogenic factors. This anti-angiogenic potency has also been shown in several animal models in which PEDF was demonstrated as the factor responsible for the reduction of blood vessel growth in the eye. Although originally discovered in the culture medium of pigment epithelial cells obtained from the fetal human retina, it is clear today that PEDF is expressed not only in the retina, but also at multiple sites in the adult eye, as well as in the adult human brain, the spinal cord, and human plasma. Therefore, it is possible that PEDF has the potential to inhibit angiogenesis throughout the body.

It is well established that protein phosphorylation plays a key role in the regulation of most intracellular processes. However, it is becoming increasingly evident that protein kinases can also regulate extracellular processes, as they are present extracellularly as either ecto- or exo-protein kinases. The ecto-protein kinases are membrane-bound enzymes whose catalytic activities are localized on the extracellular cell surface of a wide variety of cells. The exo-protein kinases are secreted, soluble enzymes whose catalytic activities are present in the extracellular environment without being directly associated to cells. These protein kinases were shown to phosphorylate both extracellular soluble substrates as well as cell surface proteins, thereby playing a regulatory role in many physiological processes including cell-cell interaction, differentiation, proliferation and ion fluxes.

In their recent work the inventors of the present invention have shown that PEDF purified from human plasma (plPEDF) is a phosphoprotein, which is phosphorylated in the circulation by casein kinase CK2 (CK2) and protein kinase A (PKA) (Maik-Rachline G., et al. Blood. 105:670-678, 2005). It was shown that CK2 phosphorylates PEDF on two main residues, Ser24 and Ser114, while PKA was shown to phosphorylate PEDF on Ser227. Using several phosphorylation site mutants that mimic either the phospho (Ser to Glu) or non-phospho (Ser to Ala) forms of PEDF, it was found that each of the CK2 and PKA phosphorylations of PEDF markedly affects its physiological function. The CK2 phosphorylated PEDF had a reduced neurotrophic activity while its anti-angiogenic activity was significantly increased. On the other hand, PKA phosphorylation reduced PEDF anti-angiogenic activity but had very little effect on its neurotrophic activity (Maik-Rachline G., et al. Blood. 2005, 105:670-678).

International Application Publication No. WO 2006/054278 to the applicants of the present invention discloses PEDF variants having substitutions of the two serine residues at the CK2 phosphorylation sites of PEDF, i.e., serine 24 and serine 114, to negatively charged amino acids which exert higher anti-angiogenic activity but lower neurotrophic activity than that of recombinant wild-type PEDF, and PEDF variants having a substitution of the serine residue at the PKA phosphorylation site, i.e., serine 227, to a negatively charged amino acid which exhibit lower anti-angiogenic activity but similar neurotrophic activity to that of recombinant wild-type PEDF. WO 2006/054278 claims anti-angiogenic variants of PEDF comprising at least one altered phosphorylation site. WO 2006/054278 further claims isolated polynucleotides encoding the anti-angiogenic variants of PEDF and methods of use thereof.

U.S. Pat. No. 5,840,686 discloses nucleic acids that encode PEDF, a truncated PEDF, and equivalent proteins, recombinant methods for producing recombinant PEDF, truncated PEDF, and equivalent proteins, and uses of these proteins in neuronal differentiation, neuron survival, and glial inhibition. U.S. Pat. No. 6,319,687 claims a recombinant PEDF protein and truncated forms of PEDF having PEDF biological activity.

International Application Publication No. WO 03/059248 discloses human plasma PEDF that exhibits potent anti-angiogenic and neurotrophic activities.

International Application Publication No. WO 2004/028559 discloses PEDF fragments consisting essentially of 5-50 contiguous amino acids of PEDF, pharmaceutical compositions comprising same and uses thereof for treating cancer or opthalomological diseases.

U.S. Patent Application No. 2005/0222031 discloses a method for preventing or treating malignant melanoma comprising administering a PEDF or a variant of PEDF, which has the functionally equivalent properties to PEDF, to a subject in need thereof. According to U.S. Patent Application No. 2005/0222031, a PEDF variant comprises an amino acid sequence that contains alteration of one or more amino acid residues in the amino acid sequence of human PEDF and has the functionally equivalent properties to human PEDF. However, nowhere in U.S. Patent Application No. 2005/0222031 the position and number of altered amino acid residues are disclosed nor the consequences of amino acid alterations on PEDF biological activity.

U.S. Pat. No. 6,821,775 discloses a replication deficient adenoviral vector comprising a nucleic acid sequence encoding PEDF or a therapeutic fragment thereof. Though suitable for incorporation into the viral vector are nucleic acid sequences comprising substitutions, deletions or additions, which encode a functioning PEDF peptide or therapeutic fragment thereof, U.S. Pat. No. 6,821,775 does not disclose specific PEDF variants capable of exerting superior activity than PEDF.

U.S. Patent Application Publication No. 2003/0158112 discloses a method of treating choroidal neovascularization comprising directly administering a therapeutic factor or a nucleic acid sequence encoding a therapeutic factor to the eye to selectively induce apoptosis of endothelial cells associated with neovascularization of the choroid, such that choroidal neovascularization is treated. Among the therapeutic factors listed is PEDF or a fragment thereof. There is no indication in U.S. Patent Application Publication No. 2003/0158112 for PEDF variants having amino acid substitutions at specific sites, which variants can be used for treating choroidal neovascularization.

International Application Publication No. WO 05/041887 discloses methods for treating conditions involving increased vascular permeability comprising administering PEDF or a PEDF 44 amino acid peptide or a homolog thereof wherein amino acid residues glutamate, isoleucine, leucine and serine at positions 101, 103, 112 and 115, respectively, are unchanged. Nowhere in International Publication Application No. WO 05/041887 it is disclosed that PEDF variants comprising substituted serine residues at positions 24, 114 and 227 can be useful for treating conditions involving increased vascular permeability or increased angiogenesis.

There is still an unmet need for potent anti-angiogenic variants of PEDF that exhibit neurotrophic activity.

SUMMARY OF THE INVENTION

The present invention provides novel anti-angiogenic PEDF variants comprising an altered amino acid sequence compared to that of human PEDF of SEQ ID NO:1 wherein the altered amino acid sequence comprises a plurality of altered phosphorylation sites. Particularly, the present invention provides novel anti-angiogenic PEDF variants comprising an altered amino acid sequence compared to that of human PEDF of SEQ ID NO:1 wherein the altered amino acid sequence comprises three altered phosphorylation sites at serine 24, serine 114, and serine 227. The present invention further provides isolated polynucleotides encoding the novel PEDF variants, pharmaceutical compositions comprising same and methods of use thereof. The present invention further provides isolated antibodies directed to the PEDF variants.

Unexpectedly, it is now disclosed that a PEDF variant comprising three negatively charged amino acid residues at positions 24, 114 and 227, replacing the naturally occurring serine residues at these positions and thus mimicking the CK2 together with the PKA phosphorylations, exhibits superior anti-angiogenic activity. This triple variant designated herein below as the EEE variant is shown to be a more potent anti-angiogenic factor than the PEDF variant comprising only two negatively charged amino acid residues at positions 24 and 114, which mimic the phosphorylation by CK2 only, and far more active than recombinant wild-type PEDF. Surprisingly, the EEE variant exhibits high neurotrophic activity. The neurotrophic activity obtained by the EEE variant was similar to that of recombinant wild-type PEDF but significantly higher than that of the PEDF variant having two negatively charged amino acid residues at serine 24 and serine 114, the latter exhibited negligible neurotrophic activity. Thus, unexpectedly the novel PEDF EEE variant exhibits superior anti-angiogenic activity while retaining the neurotrophic activity of recombinant wild-type PEDF.

It is further disclosed that a PEDF variant comprising three amino acid substitutions of serine 24, 114 and 227, of which only serine 24 and 114 are substituted by negatively charged amino acid residues, exhibits potent anti-angiogenic activity. This anti-angiogenic activity was lower than the anti-angiogenic activity exhibited by the EEE variant comprising three negatively charged amino acid residues that mimic both the CK2 and PKA phosphorylations, but similar to the anti-angiogenic activity exhibited by the PEDF variant comprising two negatively charged amino acid residues that mimic the CK2 phosphorylation only. The PEDF variant comprising three amino acid substitutions at serine 24, 114 and 227, of which only serine 24 and 114 were substituted by negatively charged amino acid residues, exerted negligible neurotrophic activity.

According to the first aspect, the present invention provides an anti-angiogenic variant of pigment epithelium derived factor (PEDF) or an analog or fusion protein thereof comprising a modified amino acid sequence derived from human PEDF of SEQ ID NO:1 or a fragment thereof comprising a plurality of altered phosphorylation sites, other than a PEDF variant or analog, fragment or fusion protein thereof consisting of only two altered phosphorylation sites at serine 24 and serine 114.

It is to be appreciated that the present invention encompasses variants of other mammalian PEDFs such as mouse, bovine, pig, and the like.

According to some embodiments, the present invention provides an anti-angiogenic variant of PEDF comprising a modified amino acid sequence derived from human PEDF of SEQ ID NO:1 comprising a plurality of altered phosphorylation sites other than a PEDF variant or analog, fragment or fusion protein thereof consisting of only two altered phosphorylation sites at serine 24 and serine 114. It is to be understood that analogs, fragments and fusion proteins of the variant of PEDF are within the scope of the present invention.

According to additional embodiments, the present invention provides an anti-angiogenic variant of PEDF comprising a variant of the amino acid sequence of human PEDF of SEQ ID NO:1 comprising a plurality of altered phosphorylation sites, with the proviso that the variant is other than a PEDF variant or analog, fragment or fusion protein thereof consisting of only two altered phosphorylation sites at serine 24 and serine 114.

According to some embodiments, the anti-angiogenic variant of PEDF, analog, fusion protein or fragment thereof comprises two altered phosphorylation sites selected from the group consisting of serine 24 and serine 227, and serine 114 and serine 227.

According to some preferred embodiments, the anti-angiogenic variant of PEDF, analog, fusion protein or fragment thereof comprises three altered phosphorylation sites at serine 24, serine 114 and serine 227.

According to further embodiments, the anti-angiogenic variant of PEDF, analog, fusion protein or fragment thereof comprising the three altered phosphorylation sites has neurotrophic activity. According to additional embodiments, the three altered phosphorylation sites of the anti-angiogenic variant of PEDF, analog, fusion protein or fragment thereof are substituted by negatively charged amino acid residues. According to an exemplary embodiment, the anti-angiogenic variant of PEDF, analog or fusion protein thereof comprises the amino acid sequence as set forth in SEQ ID NO:2 or a fragment thereof. According to a certain exemplary embodiment, the PEDF variant comprises the amino acid sequence set forth in SEQ ID NO:2.

According to additional embodiments, the anti-angiogenic variant of PEDF, analog, fusion protein or fragment thereof having neurotrophic activity comprises three altered phosphorylation sites, wherein serine 24 and serine 114 are substituted by non polar amino acid residues, and serine 227 is substituted by an amino acid residue selected from the group consisting of negatively charged amino acid and non polar amino acid residues. According to some exemplary embodiments, the anti-angiogenic variant of PEDF, analog or fusion protein thereof comprises an amino acid sequence selected from the group consisting of SEQ ID NO:3 and SEQ ID NO:4 or a fragment thereof. According to certain exemplary embodiments, the PEDF variant comprises an amino acid sequence selected from the group consisting of SEQ ID NO:3 and SEQ ID NO:4.

According to further embodiments, the anti-angiogenic variant of PEDF, analog, fusion protein or fragment thereof comprising the three altered phosphorylation sites is essentially devoid of neurotrophic activity. According to some embodiments, serine 24 and serine 114 of the anti-angiogenic variant of PEDF, analog, fusion protein or fragment thereof are substituted by negatively charged amino acid residues, and serine 227 is substituted by a non-polar amino acid residue. According to an exemplary embodiment, the anti-angiogenic variant of PEDF, analog or fusion protein thereof comprises the amino acid sequence as set forth in SEQ ID NO:5 or a fragment thereof. According to a certain exemplary embodiment, the PEDF variant comprises the amino acid sequence set forth in SEQ ID NO:5.

It is to be understood that the present invention further encompasses variants of human PEDF, analogs, fragments and fusion proteins thereof, wherein the three altered phosphorylation sites are selected from the group consisting of substitutions of serine 24 and serine 227 by negatively charged amino acid residues and substitution of serine 114 by a non-polar amino acid residue, and substitutions of serine 114 and serine 227 by negatively charged amino acid residues and substitution of serine 24 by a non-polar amino acid residue.

According to additional embodiments, the altered phosphorylation sites are obtained by a chemical modification. According to some embodiments, the chemical modification is selected from the group consisting of glycosylation, oxidation, permanent phosphorylation, reduction, myristylation, sulfation, acylation, acetylation, ADP-ribosylation, amidation, hydroxylation, iodination, methylation, and derivatization by blocking groups.

According to another aspect, the present invention provides an isolated polynucleotide sequence encoding an anti-angiogenic variant of PEDF or an analog or fusion protein thereof comprising a variant of the nucleotide sequence of human PEDF having SEQ ID NO:6 or a fragment thereof encoding the PEDF variant, analog, fragment or fusion protein thereof comprising a plurality of altered phosphorylation sites, with the proviso that the variant is other than a variant consisting of only two altered phosphorylation sites at serine 24 and serine 114.

According to some embodiments, the present invention provides an isolated polynucleotide sequence encoding an anti-angiogenic variant of PEDF comprising a variant of the nucleotide sequence of human PEDF having SEQ ID NO:6 encoding the PEDF variant comprising a plurality of altered phosphorylation sites, with the proviso that the variant is other than a variant consisting of only two altered phosphorylation sites at serine 24 and serine 114.

According to some embodiments, the isolated polynucleotide sequence encodes an anti-angiogenic variant of PEDF or an analog, fragment or fusion protein thereof comprising two altered phosphorylation sites selected from the group consisting of serine 24 and serine 227, and serine 114 and serine 227.

According to some preferred embodiments, the isolated polynucleotide sequence encodes an anti-angiogenic variant of PEDF or an analog, fragment or fusion protein thereof which comprises three altered phosphorylation sites at serine 24, serine 114 and serine 227.

According to some embodiments, the anti-angiogenic variant of PEDF, analog, fragment or fusion protein thereof comprising the three altered phosphorylation sites encoded by the isolated polynucleotide sequence has neurotrophic activity. According to additional embodiments, the three altered phosphorylation sites of the anti-angiogenic variant of PEDF, analog, fragment or fusion protein thereof encoded by the isolated polynucleotide sequence are substituted by negatively charged amino acid residues. According to an exemplary embodiment, the isolated polynucleotide sequence encoding the anti-angiogenic variant of PEDF or an analog or fusion protein thereof comprising the three altered phosphorylation sites substituted by negatively charged amino acid residues comprises SEQ ID NO:7 or a fragment thereof. According to a certain exemplary embodiment, the isolated polynucleotide sequence encoding the PEDF variant comprises the nucleotide sequence set forth in SEQ ID NO:7.

According to additional embodiments, the isolated polynucleotide sequence encodes an anti-angiogenic variant of PEDF or an analog, fragment or fusion protein thereof comprising three altered phosphorylation sites, wherein serine 24 and serine 114 of the anti-angiogenic variant of PEDF, analog, fragment or fusion protein thereof are substituted by non polar amino acid residues, and serine 227 is substituted by an amino acid residue selected from the group consisting of negatively charged amino acid and non polar amino acid residues. According to some exemplary embodiments, the isolated polynucleotide sequence encoding the anti-angiogenic variant of PEDF or an analog or fusion protein thereof comprises the nucleotide sequence selected from the group consisting of SEQ ID NO: 8 and SEQ ID NO:9 or a fragment thereof. According to certain exemplary embodiments, the isolated polynucleotide sequence encoding the PEDF variant comprises the nucleotide sequence as set forth in SEQ ID NO:8 or SEQ ID NO:9.

According to further embodiments, the anti-angiogenic variant of PEDF, analog, fragment or fusion protein thereof comprising three altered phosphorylation sites encoded by an isolated polynucleotide sequence is essentially devoid of neurotrophic activity. According to some embodiments, the isolated polynucleotide sequence encodes an anti-angiogenic variant of PEDF or an analog, fragment or fusion protein thereof, wherein serine 24 and serine 114 of the anti-angiogenic variant of PEDF, analog, fragment or fusion protein thereof are substituted by negatively charged amino acid residues and serine 227 is substituted by a non-polar amino acid residue. According to an exemplary embodiment, the isolated polynucleotide sequence encoding the anti-angiogenic variant of PEDF, analog or fusion protein thereof comprises the nucleotide sequence as set forth in SEQ ID NO:10 or a fragment thereof. According to a certain exemplary embodiment, the isolated polynucleotide sequence encoding the PEDF variant comprises a nucleotide sequence as set forth in SEQ ID NO:10.

According to a further aspect, the present invention provides an expression vector comprising an isolated polynucleotide sequence encoding an anti-angiogenic variant of PEDF or an analog, fragment or fusion protein thereof according to the principles of the present invention.

According to yet further aspect, the present invention provides a host cell comprising an expression vector comprising an isolated polynucleotide sequence encoding an anti-angiogenic variant of PEDF or an analog, fragment or fusion protein thereof according to the principles of the present invention.

According to an additional aspect, the present invention provides a pharmaceutical composition comprising as an active ingredient an anti-angiogenic variant of PEDF or an analog, fusion protein or fragment thereof according to the principles of the present invention and a pharmaceutically acceptable carrier.

According to further aspect, the present invention provides a pharmaceutical composition comprising as an active ingredient an isolated polynucleotide sequence encoding an anti-angiogenic variant of PEDF or an analog, fusion protein or fragment thereof according to the principles of the present invention and a pharmaceutically acceptable carrier.

According to yet another aspect, the present invention provides a pharmaceutical composition comprising as an active ingredient an expression vector comprising an isolated polynucleotide sequence encoding an anti-angiogenic variant of PEDF or an analog, fusion protein or fragment thereof according to the principles of the present invention and a pharmaceutically acceptable carrier.

According to further aspect, the present invention provides a pharmaceutical composition comprising as an active ingredient a host cell comprising an expression vector comprising an isolated polynucleotide sequence encoding an anti-angiogenic variant of PEDF or an analog, fusion protein or fragment thereof according to the principles of the present invention and a pharmaceutically acceptable carrier.

According to another aspect, the present invention provides a method for treating a disease or disorder associated with neovascularization in a subject comprising administering to the subject in need thereof a therapeutically effective amount of a pharmaceutical composition according to the principles of the present invention.

According to some embodiments, the disease or disorder associated with neovascularization is selected from the group consisting of cancer, ocular disorders, and disorders treated with anti-angiogenic factors.

According to additional embodiments, the disease or disorder associated with neovascularization is cancer selected from the group consisting of sarcoma, carcinoma, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor leiomydsarcoma, rhabdomyosarcoma, colon carcinoma, pancreatic cancer, breast cancer, ovarian cancer, prostate cancer, squamous cell carcinoma, basal cell carcinoma, adenocarcinoma sweat gland carcinoma, sebaceous gland carcinoma, papillary carcinoma, papillary adenocarcinoma, cystadenocarcinoma, medullary carcinoma, bronchogenic carcinoma, renal cell carcinoma, hepatoma bile duct carcinoma, choriocarcinoma, seminoma, embryonal carcinoma, Wilms' tumor cervical cancer, testicular tumor, lung carcinoma, small cell lung carcinoma, bladder carcinoma, epithelial carcinoma, glioma, astrocytoma, medulloblastoma, craniopharyngioma, ependymoma, Kaposi's sarcoma, pinealoma, hemangioblastoma, acoustic neuroma, oligodendroglioma, menangioma, melanoma and neuroblastoma.

According to additional embodiments the ocular disorder to be treated by the method of the present invention is selected from the group consisting of neovascular glaucoma, diabetic retinopathy, retinoblastoma, retrolental fibroplasias, uveitis, retinopathy of prematurity, macular degeneration, corneal graft neovascularization, retinal tumors and choroidal tumors. According to further embodiments, the disorder which is treated with anti-angiogenic factors is selected from the group consisting of hemangioma, arthritis, psoriasis, angiofibroma, atherosclerotic plaques, hemophilic joints, and hypertrophic scars.

According to further aspect, the present invention provides a method for treating a neurodegenerative condition in a subject comprising administering to the subject in need thereof a therapeutically effective amount of a pharmaceutical composition according to the principles of the present invention.

According to some embodiments, the neurodegenerative condition is selected from the group consisting of multiple sclerosis, Alzheimer's disease, Parkinson's disease, myasthenia gravis, motor neuropathy, Guillain-Barre syndrome, autoimmune neuropathy, Lambert-Eaton myasthenic syndrome, paraneoplastic neurological disease, paraneoplastic cerebellar atrophy, non-paraneoplastic stiff man syndrome, progressive cerebellar atrophy, Rasmussen's encephalitis, amyotrophic lateral sclerosis, Sydeham chorea, Tourette syndrome, autoimmune polyendocrinopathy, dysimmune neuropathy, acquired neuromyotonia, arthrogryposis multiplex, optic neuritis and stiff-man syndrome.

According to another aspect, the present invention provides an isolated antibody or fragment thereof which specifically binds to a polypeptide selected from: (a) an anti-angiogenic variant of PEDF comprising a modified amino acid sequence derived from human PEDF of SEQ ID NO:1 which comprises at least one altered phosphorylation site negatively charged; (b) a fragment of (a); and (c) an analog of (a) or (b), wherein the isolated antibody does not bind to the corresponding amino acid sequence of human PEDF of SEQ ID NO:1 having a non-phosphorylated serine or an altered phosphorylation site not negatively charged.

According to some embodiments, the present invention provides an isolated antibody or fragment thereof which specifically binds to a variant of the amino acid sequence of human PEDF of SEQ ID NO:1 which comprises at least one altered phosphorylation site negatively charged, wherein the isolated antibody does not bind to the corresponding amino acid sequence of human PEDF of SEQ ID NO:1 having a non-phosphorylated serine or an altered phosphorylation site not negatively charged.

According to additional embodiments, the isolated antibody or fragment thereof specifically binds to a PEDF variant or a fragment or analog thereof which comprises one altered phosphorylation site at serine 24. According to exemplary embodiments, the isolated antibody or fragment thereof specifically binds to a PEDF variant comprising the amino acid sequence selected from the group consisting of SEQ ID NOs: 2, 5, 11 and 12.

According to further embodiments, the isolated antibody or fragment thereof specifically binds to a PEDF variant or a fragment or analog thereof which comprises one altered phosphorylation site at serine 227. According to exemplary embodiments, the isolated antibody or fragment thereof specifically binds to a PEDF variant comprising the amino acid sequence selected from the group consisting of SEQ ID NOs: 2, 3 and 13.

According to additional embodiments, the isolated antibody or fragment thereof specifically binds to a PEDF variant or a fragment or analog thereof which comprises one altered phosphorylation site at serine 114. According to exemplary embodiments, the isolated antibody or fragment thereof specifically binds to a PEDF variant comprising the amino acid sequence selected from the group consisting of SEQ ID NOs: 2, 5, 12 and 14.

According to further embodiments, the isolated antibody or fragment thereof specifically binds to a PEDF variant or a fragment or analog thereof which comprises two altered phosphorylation sites at serine 24 and serine 114. According to exemplary embodiments, the isolated antibody or fragment thereof specifically binds to a PEDF variant comprising the amino acid sequence selected from the group consisting of SEQ ID NOs:2, 5 and 12.

According to yet further embodiments, the isolated antibody or fragment thereof specifically binds to a PEDF variant or a fragment or analog thereof which comprises three altered phosphorylation sites at serine 24, serine 114 and serine 227. According to exemplary embodiments, the isolated antibody or fragment thereof specifically binds to a PEDF variant comprising the amino acid sequence of SEQ ID NOs:2.

According to additional embodiments, the isolated antibody or fragment thereof is selected from the group consisting of a polyclonal antibody, a monoclonal antibody, a Fab, a F(ab)2, a chimeric antibody, and a single chain antibody.

According to a further aspect, the present invention provides methods for producing the PEDF variants of the present invention comprising culturing prokaryotic and/or eukaryotic host cells comprising a polynucleotide encoding a PEDF variant or a fragment or analog thereof of the present invention under conditions promoting expression of said variant, fragment or analog and subsequent recovery of the variant, fragment or analog.

These and other embodiments of the present invention will be better understood in relation to the figures, description, examples and claims that follow.

BRIEF DESCRIPTION OF THE FIGURES

FIGS. 1A-D show the interplay between the CK2 and PKA phosphorylations of PEDF. FIG. 1A, recombinant PEDF (rPEDF) and S24,114E variant (EE) pre-dialyzed in different pH buffers (indicated) were phosphorylated by PKA. SDS gel was stained with Coomassie blue (lower panel) and subjected to autoradiography (upper panel). FIG. 1B, The experiment in FIG. 1A was performed with rPEDF and S24,114E variant (EE) that were subjected to heat treatment prior to phosphorylation. FIG. 1C, rPEDF and S24,114A variant (AA) pre-dialyzed in different pH buffers (indicated) were phosphorylated by PKA with or without heat-treatment prior to the phosphorylation. Phosphorylated products were analyzed by SDS-PAGE and autoradiography (upper panel) or by immunoblotting with anti-PEDF antibodies (lower panel). FIG. 1D, plasma PEDF (plPEDF), rPEDF, S227A and S227E variants were phosphorylated by CK2 with or without heat-treatment prior to the phosphorylation. Phosphorylated products were analyzed as described in panel FIG. 1A.

FIGS. 2A-C show in vitro CK2 and PKA phosphorylation of PEDF. FIG. 2A shows a schematic representation of PEDF variants wherein Ser24, Ser114 and/or Ser227 were substituted to Ala or Glu. FIGS. 2B and 2C, rPEDF and rPEDF variants were phosphorylated by CK2 (FIG. 2B) or by PKA (FIG. 2C) and the phosphorylated products were analyzed by SDS-PAGE followed by autoradiography (upper panels) and immunoblotting with anti-PEDF antibodies (lower panels).

FIG. 3A, HUVEC were stimulated with the indicated rPEDF variants. Cytosolic extracts were subjected to immunoblotting with anti-phospho ERK antibodies (αpERK, upper panel) or anti-general ERK antibodies (αgERK, lower panel). The positions of ERK2 and ERK1 are indicated. FIG. 3B, Quantitative analysis of the results in FIG. 1A, presented as ERK activation for both ERK1 and ERK2. FIG. 3C, HUVEC were incubated with plasma (pl) PEDF, rPEDF or PEDF variants. After 48 hrs cell number was determined by methylene blue assay.

FIG. 4A, Retinoblastoma Y-79 cells were incubated with rPEDF or the rPEDF variants. Cell morphology was visualized by an inverted microscope 7 days after cell attachment onto poly-D-lysine coated plates. FIG. 4B, Quantitative analysis of the results presented in panel FIG. 4A. *P<0.01; **P<0.05 indicate a comparison between cells treated with rPEDF and cells treated with the various PEDF variants.

FIG. 5A, CD-1 nude mice were subcutaneously injected with 0.5 ml Matrigel containing rPEDF, plPEDF, and the PEDF variants in the presence or absence of bFGF (300 ng/ml). Control plugs were treated with PBS or bFGF only. After 7 days, mice were sacrificed and the plugs were subjected to H&E staining and photographed under light microscope (×40 magnification). FIG. 5B, Angiogenesis was quantified by counting number of blood vessels/field for 3 different cross sectional areas. *P<0.01 indicates statistical significance of the differences between plugs treated with bFGF and plugs treated with both bFGF and a PEDF variant.

FIG. 6A, CD-1 nude mice were subcutaneously injected with 0.5 ml Matrigel containing PEDF variants in the presence or absence of bFGF (500 ng/ml). Control plugs were treated with PBS or bFGF only. After 7 days, mice were sacrificed and the plugs were stained with H&E and photographed under light microscope (×40 magnification). FIG. 6B, Angiogenesis was quantified by counting number of blood vessels/field for 3 different cross sectional areas. **P<0.05 indicates statistical significance of the differences between plugs treated with bFGF and EEE variant and plugs treated with bFGF and EEA or the S24,114E variant.

FIG. 8A, CD-1 nude mice implanted with DU145 cells were treated with the EEE variant. The control group was treated with PBS. Fold increase in tumor volume vs. its initial size is presented. FIG. 8B, Pictures of tumors at day 36. Left side, tumors excised from the PBS treated group. Right side, tumors excised from the EEE variant treated group.

FIG. 9A, Recombinant PEDF (r) or plasma PEDF (pl) were subjected to immunoblotting with αpSer24, αpSer227 or with αPEDF antibodies. FIG. 9B, rPEDF or plPEDF were treated with potato acid phosphatase (PAP) and then subjected to immunoblotting with αpSer24, αpSer227 or with αPEDF antibodies. Control samples were left untreated. FIG. 9C, rPEDF, EEA, AAE, EEE or AAA variants were subjected to immunoblotting with αpSer24, αpSer227 or with αPEDF antibodies.

DETAILED DESCRIPTION OF THE INVENTION

Figure 3A:
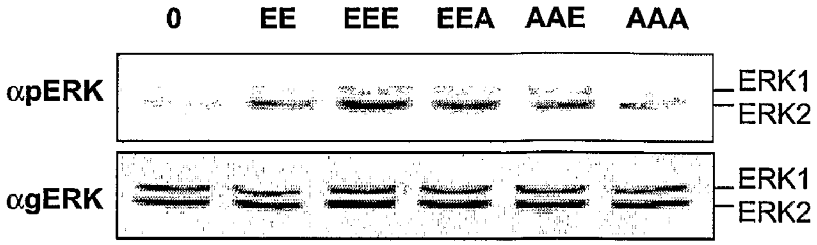
FIGS. 3A-C show the effect of rPEDF variants on ERK activation and proliferation in human umbilical vascular endothelial cells (HUVEC).

The present invention provides anti-angiogenic PEDF variants, fragments, analogs, and fusion proteins thereof comprising a plurality of altered phosphorylation sites. The invention also provides isolated nucleic acids encoding PEDF variants, fragments, analogs and fusion proteins thereof, the PEDF variants, fragments, analogs and fusion proteins thereof comprising a plurality of altered phosphorylation sites and having anti-angiogenic activity.

According to the present invention, the naturally occurring human PEDF of SEQ ID NO:1 contains two CK2 and one PKA phosphorylation sites. The CK2 phosphorylation sites reside at serine residues 24 and 114, while the PKA phosphorylation site resides at serine residue at position 227.

According to one aspect, the present invention provides an isolated anti-angiogenic variant of PEDF, analog, or a fusion protein thereof comprising the amino acid sequence of SEQ ID NO:1 or a fragment thereof comprising a plurality of altered phosphorylation sites.

The term "PEDF variant" refers herein to a PEDF protein comprising a modified or altered amino acid sequence compared to the naturally occurring PEDF wherein at least two, preferably at least three phosphorylation sites being altered, which variant retains anti-angiogenic activity. It will be understood that the present invention particularly relates to human PEDF of SEQ ID NO:1, however as there is high homology between human PEDF and PEDF derived from other mammalian species, the present invention encompasses other mammalian PEDFs such as mouse, bovine, pig, and the like.

The PEDF variant is typically provided in an isolated form. The term "isolated" means that the variant is separated from other biological components which naturally accompany a native sequence, e.g., proteins, polynucleotides, and the like. Preferably, the PEDF variant is purified to homogeneity.

The term "plurality" of altered phosphorylation sites refers to at least two altered phosphorylation sites, preferably at least three altered phosphorylation sites.

According to some embodiments, the anti-angiogenic variant of PEDF, analog, or a fusion protein thereof comprises two phosphorylation sites selected from the group consisting of serine 24 and serine 227, and serine 114 and serine 227. PEDF variants comprising altered phosphorylation sites on both serine 24 and serine 114 are excluded from the present invention.

According to some preferred embodiments, the anti-angiogenic variant of PEDF, analog, fragment or a fusion protein thereof comprises three altered phosphorylation sites at serine 24, serine 114 and serine 227.

According to some embodiments, the present invention provides a PEDF variant, fragment, analog, or a fusion protein thereof having reduced neurotrophic activity compared to wild-type recombinant PEDF. Preferably, the PEDF variant, fragment or analog thereof has neurotrophic activity.

The term "fragment" as used herein refers to any portion of the full length amino acid sequence of PEDF which has less amino acids than the full length amino acid sequence of PEDF, e.g., less than the 418 amino acids of human PEDF of SEQ ID NO:1, which portion still contains a plurality of altered phosphorylation sites and still retains anti-angiogenic activity. Typically, a portion of a full length protein is a peptide, polypeptide or protein. By "peptide" it is meant that an amino acid sequence consisting of not more than 50 amino acids. By "polypeptide" it is meant an amino acid sequence generally consisting of more than 50 amino acid residues. By "protein" it is meant one or more covalently attached polypeptide chains. The terms peptide, polypeptide and protein are used interchangeable throughout the specification.

The term "anti-angiogenic" activity used herein is meant to define the ability of PEDF variant to reduce or inhibit endothelial cell proliferation and/or to reduce or inhibit endothelial cell migration and/or to induce endothelial cell apoptosis, and/or to reduce or inhibit neovascularization. Anti-angiogenic activity may be detected by various methods known in the art. Examples of in vitro or in vivo assays for detecting angiogenic or anti-angiogenic activity include mouse corneal neovascularization, chick chorioallantoic membrane assay, rabbit corneal pocket assay, aortic ring assay, and neovascularization in Matrigel plug assay (see also examples herein below).

The term "analog" as used herein refers to a PEDF peptide, polypeptide or protein having a modified amino acid sequence as compared to the naturally occurring PEDF preferably human PEDF of SEQ ID NO:1, which comprises a plurality of altered phosphorylation sites and at least one amino acid substitution, addition, deletion, and/or chemical modification. By using "amino acid substitution", it is meant that functionally equivalent amino acid residue is substituted for a residue within the sequence resulting in a silent change. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the non-polar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such substitutions are known as conservative substitutions. Additionally, the present invention encompasses non-conservative substitutions. Non-conservative substitutions can be made so that the biological activity e.g., anti-angiogenic activity, of a PEDF variant, analog or fragment thereof be retained or alternatively be improved. It will be appreciated that the present invention encompasses PEDF analogs, wherein at least two amino acid residues are substituted by other amino acid to produce an anti-angiogenic analog of PEDF variant having increased stability or higher half life as compared to the naturally occurring PEDF or the wild-type recombinant PEDF.

The analogs of the present invention include peptides, polypeptides or proteins which have at least 70% similarity to human PEDF of SEQ ID NO:1 or a fragment thereof, preferably at least 80% homology to human PEDF of SEQ ID NO:1 or a fragment thereof, still more preferably at least 90% homology to human PEDF of SEQ ID NO:1 or a fragment thereof, and most preferably at least 95% homology to human PEDF of SEQ ID NO:1 or a fragment thereof. The term "similarity" between two polypeptides is determined by comparing the amino acid sequence and its conserved amino acid substitutes of one polypeptide to the sequence of a second polypeptide.

The term "altered phosphorylation site" as used herein refers to an alteration of a phosphorylation site by an amino acid substitution and/or by chemical modification. It will be appreciated that substitution of a serine or threonine residue within a phosphorylation site is meant to refer to a conservative, but preferably to a non-conservative, substitution. Thus, substitution of a serine residue residing within a phosphorylation site of CK2 or PKA includes substitution to a non-polar amino acid, to a negatively charged amino acid, or to a positively charged amino acid, preferably to a negatively charged amino acid. The term "modified amino acid" as used herein refers to an amino acid alteration by amino acid substitution and/or by chemical modification. The terms altered and modified are used interchangeably throughout the specification and claims.

Since phosphorylation of a serine residue within a protein is associated with addition of a negatively charged phosphate group to that serine, substitution of a serine by a negatively charged amino acid mimics the phosphorylated serine and is thus useful to characterize the biological significance of that phosphorylation. Importantly, while a phosphorylated protein is dephosphorylated through phosphatases activity in vivo, substitution of a serine with a negatively charged amino acid yields a protein having a permanent negatively charged amino acid at that site.

As shown herein below, substitutions of the serine residues at position 24, 114 and 227 of recombinant human PEDF by glutamic acid residues resulted in a PEDF variant having high anti-angiogenic and neurotrophic activity. Substitution of serine residues at positions 24 and 114 to glutamic acid while substituting serine residue at position 227 to alanine resulted in a PEDF variant having anti-angiogenic activity but almost devoid of neurotrophic activity. Substitution of seine residues at positions 24 and 114 to alanine while substituting serine residue at position 227 to glutamic acid resulted in a PEDF variant having lower neurotrophic activity but similar anti-angiogenic activity to that of recombinant wild-type PEDF. Substitution of all three serine residues to alanine resulted in a PEDF variant having similar neurotrophic and anti-angiogenic activities as of recombinant wild-type PEDF.

The term "neurotrophic" activity is defined herein as the ability to induce differentiation to a neuronal cell phenotype. For example, PEDF's ability to induce differentiation in cultured retinoblastoma cells is considered neurotrophic activity. A PEDF variant, fragment, analog or a fusion protein thereof may be essentially devoid of neurotrophic activity. By referring to essentially devoid of neurotrophic activity it is meant to indicate that the PEDF variant, fragment, analog or fusion protein thereof has not more than 20% of the neurotrophic activity of recombinant wild-type PEDF, preferably not more than 10%, and more preferably not more than 5% of the neurotrophic activity of recombinant wild-type PEDF.

The present invention encompasses PEDF variants, analogs, fragments or fusion proteins thereof which comprise chemically modified amino acid residues. Modifications of amino acid residues include, but are not limited to, glycosylation, oxidation, permanent phosphorylation, reduction, myristylation, sulfation, acylation, acetylation, ADP-ribosylation, amidation, cyclization, disulfide bond formation, hydroxylation, iodination, methylation, derivatization by protecting/blocking groups, or any other derivatization method known in the art. Such modifications can occur anywhere along the sequence of the PEDF variant, analog or fragment thereof, including at the peptide backbone, the amino acid side-chains, the amino or carboxyl termini.

The PEDF variants, fragments and analogs thereof comprising a plurality of altered phosphorylation sites can be produced by various methods known in the art, including recombinant production or synthetic production. Recombinant production can be achieved by the use of an isolated polynucleotide encoding a PEDF variant, fragment or analog thereof, the isolated polynucleotide operably linked to a promoter for the expression of the polynucleotide. Optionally, a regulator of the promoter, a ribosome binding site, a translation initiation and transcription terminator are added. A construct comprising the polynucleotide encoding the PEDF variant, fragment or analog thereof, the promoter, and optionally the regulator, the ribosome binding site, the translation initiation and the transcription terminator can be placed in a vector, such as a plasmid, virus or phage vector. The vector can be used to transfect or transform a host cell, e.g., a bacterial, yeast, insect, or mammalian cell.

The present invention also encompasses PEDF fragments produced by subjecting the PEDF variant or an analog thereof to at least one cleavage agent. A cleavage agent may be a chemical cleavage agent, e.g., cyanogen bromide, or an enzyme, preferably an endoproteinase. Endoproteinases that can be used to cleave the PEDF variant or analog thereof include trypsin, chymotrypsin, papain, V8 protease or any other enzyme known in the art to produce proteolytic fragments.

Synthetic production of peptides, polypeptides or proteins is well known in the art and is available commercially from a variety of companies. A PEDF variant, fragment or an analog thereof comprising a plurality of altered phosphorylation sites can be synthesized using standard direct peptide synthesis (see Bodanszky, 1984, Principles of Peptide Synthesis, Springer-Verlag, Heidelberg) such as via solid-phase synthesis (see, e.g., Merrifield, 1963, J. Am. Chem. Soc. 85:2149-2154). Examples of solid phase peptide synthesis methods include the BOC method, which utilizes tert-butyloxycarbonyl as the α-amino protecting group, and the FMOC method, which utilizes 9-fluorenylmethyloxycarbonyl to protect the α-amino of the amino acid residues, both methods are well known to skilled in the art. Furthermore, if desired, non-classical amino acids or chemical amino acid analogs can be introduced as a substitution or addition into a PEDF variant, fragment or analog thereof. Non-classical amino acids include, but are not limited to, oc-aminoisobutyric acid, 4-aminobutyric acid, hydroxyproline, sarcosine, citrulline, cysteic acid, t-butylglycine, t-butylalanine, phenylglycine, cyclohexylalanine, and the like.

The invention further encompasses PEDF variants, fragments or analogs thereof, which can contain one or more D-isomer forms of the amino acids of PEDF. Production of a retro-inverso D-amino acid PEDF peptide where the peptide is made with the same amino acids as disclosed, but at least one amino acid, and perhaps all amino acids are D-amino acids is a simple matter once armed with the present invention. When all of the amino acids in the peptide are D-amino acids, and the N- and C-terminals of the molecule are reversed, the result is a molecule having the same structural groups being at the same positions as in the L-amino acid form of the molecule. However, the molecule is more stable against proteolytic degradation and is therefore useful in many of the applications recited herein.

Included within the scope of the invention are chimeric, or fusion proteins comprising a PEDF variant, a fragment or analog thereof joined at its amino or carboxy-terminus or at one of the side chains via a peptide bond to an amino acid sequence of a different protein. Such chimeric proteins can be made by protein synthesis, e.g., by use of a peptide synthesizer, or by ligating the appropriate nucleic acid sequences encoding the desired amino acid sequences to each other by methods known in the art, in the proper coding frame, and expressing the chimeric protein by methods commonly known in the art.

According to another aspect, the present invention provides an isolated polynucleotide sequence comprising a modified nucleotide sequence derived from the nucleotide sequence of human PEDF of SEQ ID NO:6 which encodes an anti-angiogenic variant of PEDF or a fragment, analog, or fusion protein thereof comprising a modified amino acid sequence derived from SEQ ID NO:1 comprising a plurality of altered phosphorylation sites, with the proviso that the isolated polynucleotide sequence does not encode a PEDF variant, fragment, analog or fusion protein thereof comprising a modified amino acid sequence compared to SEQ ID NO:1 consisting of only two altered phosphorylation sites on serine 24 and serine 114. For sake of brevity, the term "PEDF variant" used herein below in the description should be construed to include all forms of PEDF variants including analogs, fragments and fusion proteins thereof that comprise a plurality of altered phosphorylation sites and having anti-angiogenic activity.

It is to be understood that the terms "modified nucleotide sequence" and "variant of a nucleotide sequence" as used herein refer to an altered nucleotide sequence compared to that of human PEDF set forth in SEQ ID NO:6, preferably by nucleotide substitution which results in a different amino acid within a phosphorylation site.

The term "polynucleotide" means a polymer of deoxyribonucleic acid (DNA) or ribonucleic acid (RNA), which can be derived from any source, can be single- or double-stranded, and can optionally contain synthetic, non-natural, or altered nucleotides, which are capable of being incorporated into DNA or RNA polymers.

An "isolated polynucleotide" refers to a polynucleotide segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to polynucleotides, which have been substantially purified from other components, which naturally accompany a nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA, which is part of a hybrid gene encoding an additional polypeptide sequence, and RNA such as mRNA.

The term "encoding" refers to the inherent property of specific sequences of nucleotides in an isolated polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a polypeptide or protein if transcription and translation of mRNA corresponding to that gene produces the polypeptide or protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the polypeptide or protein or other product of that gene or cDNA.

One who is skilled in the art will appreciate that more than one nucleic acid may encode any given polypeptide or protein in view of the degeneracy of the genetic code and the allowance of exceptions to classical base pairing in the third position of the codon, as given by the so-called "Wobble rules". Moreover, polynucleotides that include more or less nucleotides can result in the same or equivalent polypeptides or proteins. Accordingly, it is intended that the present invention encompasses polynucleotides that encode the amino acid sequences of SEQ ID NO:2 to SEQ ID NO:5, as well as analogs, fragments or fusion proteins thereof.

The polynucleotides of the present invention can also have the coding sequence fused in frame to a marker sequence which allows for purification of the polypeptide of the present invention. The marker sequence can be a six histidine tag in the case of a bacterial host or hemagglutinin (HA) tag in the case of a mammalian host.

Polynucleotide sequences which encode wild type or native PEDF protein are known (see, e.g., published International Patent Applications WO 95/33480 and WO 93/24529), and others can be deduced from the polypeptide sequences discussed herein. According to specific embodiments, the present invention provides polynucleotide sequences encoding PEDF variants selected from SEQ ID NO:7 to SEQ ID NO:10.

The PEDF polynucleotides may be expressed as a transported protein where the PEDF variant is isolated from the medium in which the host cell containing the polynucleotide is grown, or may be expressed as an intracellular protein by deleting the leader or other peptides, in which case the PEDF is isolated from the host cells. The PEDF so isolated is then purified by protein purification methods known in the art.

PEDF variants, analogs or fragments thereof can be provided to the tissue of interest by transferring an expression vector comprising an isolated polynucleotide encoding a PEDF variant, fragment or analog thereof to cells associated with the tissue of interest. The cells produce and secrete the PEDF polypeptide variant such that it is suitably provided to cells within the tissue to exert biological activity such as anti-angiogenic activity or neurotrophic activity, within the tissue of interest. Thus, the expression vectors comprising a PEDF variant typically include isolated polynucleotide sequences which are homologous to known PEDF sequences, e.g., they will hybridize to at least a fragment of the known sequences under at least mild stringency conditions, more preferably under moderate stringency conditions, most preferably under high stringency conditions (employing the definitions of mild, moderate, and high stringency as set forth in Sambrook et al., 1989, Molecular Cloning: A Laboratory Manual, 2d edition, Cold Spring Harbor Press).

In addition to the isolated polynucleotide sequences encoding PEDF variant polypeptides, the expression vectors comprise a promoter. In the context of the present invention, the promoter must be able to drive the expression of the PEDF polynucleotide within the cells. Many viral promoters are appropriate for use in such an expression cassette e.g., retroviral ITRs, LTRs, immediate early viral promoters (IEp) such as herpes virus IEp (e.g., ICP4-IEp and ICP0-IEp) and cytomegalovirus (CMV) IEp, and other viral promoters (e.g., late viral promoters, latency-active promoters (LAPs), Rous Sarcoma Virus (RSV) promoters, and Murine Leukemia Virus (MLV) promoters). Other suitable promoters are eukaryotic promoters, which contain enhancer sequences (e.g., the rabbit β-globin regulatory elements), constitutively active promoters (e.g., the β-actin promoter, etc.), signal and/or tissue specific promoters (e.g., inducible and/or repressible promoters, such as a promoter responsive to TNF or RU486, the metallothionine promoter, etc.), and tumor-specific promoters.

Within the expression vector, the polynucleotide encoding the PEDF variant or an analog or fragment thereof and the promoter are operably linked such that the promoter is able to drive the expression of the polynucleotide encoding the PEDF variant, analog or fragment thereof. As long as this operable linkage is maintained, the expression vector can include more than one gene, such as multiple genes separated by internal ribosome entry sites (IRES). Furthermore, the expression vector can optionally include other elements, such as splice sites, polyadenylation sequences, transcriptional regulatory elements (e.g., enhancers, silencers, etc.), or other sequences.

The expression vectors must be introduced into the cells in a manner such that they are capable of expressing the isolated polynucleotide encoding a PEDF variant, a fragment or analog thereof contained therein. Any suitable vector can be so employed, many of which are known in the art. Examples of such vectors include naked DNA vectors (such as oligonucleotides or plasmids), viral vectors such as adeno-associated viral vectors (Berns et al., 1995, Ann. N.Y. Acad. Sci. 772: 95-104), adenoviral vectors, herpes virus vectors (Fink et al., 1996, Ann. Rev. Neurosci. 19:265-287), packaged amplicons (Federoff et al., 1992, Proc. Natl. Acad. Sci. USA 89:1636-1640), papilloma virus vectors, picornavirus vectors, polyoma virus vectors, retroviral vectors, SV40 viral vectors, vaccinia virus vectors, and other vectors. In addition to the expression vector of interest, the vector can also include other genetic elements, such as, for example, genes encoding a selectable marker (e.g., β-gal or a marker conferring resistance to a toxin), a pharmacologically active protein, a transcription factor, or other biologically active substance.

Methods for manipulating a vector comprising an isolated polynucleotide are well known in the art (see, e.g., Sambrook et al., supra) and include direct cloning, site specific recombination using recombinases, homologous recombination, and other suitable methods of constructing a recombinant vector. In this manner, an expression vector can be constructed such that it can be replicated in any desired cell, expressed in any desired cell, and can even become integrated into the genome of any desired cell.

The PEDF variant expression vector is introduced into the cells by any means appropriate for the transfer of DNA into cells. Many such methods are well known in the art (Sambrook et al., supra; see also Watson et al., 1992, Recombinant DNA, Chapter 12, 2d edition, Scientific American Books). Thus, in the case of prokaryotic cells, vector introduction may be accomplished, for example, by electroporation, transformation, transduction, conjugation, or mobilization. For eukaryotic cells, vectors may be introduced through the use of, for example, electroporation, transfection, infection, DNA coated microprojectiles, or protoplast fusion.

Cells, into which the PEDF variant polynucleotide has been transferred under the control of an inducible promoter if necessary, can be used as transient transformants. Such cells themselves may then be transferred into a mammal for therapeutic benefit therein. Typically, the cells are transferred to a site in the mammal such that the PEDF variant expressed therein and secreted therefrom contacts the desired cells, e.g., endothelial cells, in order that the PEDF activity is exerted, e.g., angiogenesis is inhibited. Alternatively, particularly in the case of cells to which the vector has been added in vitro, the cells may first be subjected to several rounds of clonal selection (facilitated usually by the use of a selectable marker sequence in the vector) to select for stable transformants. Such stable transformants are then transferred to a mammal for therapeutic benefit therein.

The PEDF variant may also be provided to cells, e.g., endothelial cells, by transfecting into a population of other cells a vector comprising an isolated polynucleotide encoding a PEDF variant according to the invention, whereby the PEDF variant is expressed in and secreted from said other cells. The population of other cells so transfected is then transferred to a site in the mammal where PEDF variant so secreted contacts the cells, e.g., endothelial cells, and inhibits angiogenesis. Expression and secretion of PEDF variant from the other cells then has benefit on the cells of interest. It is not necessary that the polynucleotide encoding a PEDF variant be stably integrated into the cells. PEDF variant may be expressed and secreted from non-integrated or from integrated polynucleotide in a cell.

Within the cells, the PEDF variant polynucleotide is expressed such that the cells express and secrete the PEDF variant polypeptide. Successful expression of the polynucleotide can be assessed using standard molecular biology techniques (e.g., Northern hybridization, Western blotting, immunoprecipitation, enzyme immunoassay, etc.). Reagents for detecting the expression of PEDF genes and the secretion of PEDF variants from transfected cells are known in the art (see also examples herein below).

The PEDF variants produced by recombinant techniques may be purified so that the PEDF variant will be substantially pure when administered to a subject. The term "substantially pure" refers to a compound, e.g., a protein or polypeptide, which has been separated from components, which naturally accompany it. Typically, a compound is substantially pure when at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides or proteins by column chromatography, gel electrophoresis or HPLC analysis. A compound, e.g., a polypeptide or protein, is also substantially purified when it is essentially free of naturally associated components or when it is separated from the native contaminants which accompany it in its natural state.

Antibodies

A number of immunogens can be used to produce antibodies specifically reactive with a PEDF variant comprising a plurality of altered phosphorylation sites. Recombinant full length PEDF variant or a fragment thereof can be used for the production of antibodies. Synthetic peptides derived from PEDF variant protein sequences described herein can also be used as an immunogen for the production of antibodies (see Example 8 herein below). Recombinant protein can be expressed in eukaryotic or prokaryotic cells, purified and used as an immunogen. Naturally folded or denatured protein can be used, as appropriate, for producing antibodies. Either monoclonal or polyclonal antibodies may be generated.

It should be understood that when the terms "antibody" or "antibodies" are used, this is intended to include intact antibodies, such as polyclonal antibodies or monoclonal antibodies (mAbs), as well as proteolytic fragments thereof such as the Fab or $F(ab')_2$ fragments. Further included within the scope of the invention are chimeric antibodies; human and humanized antibodies; recombinant and engineered antibodies, and fragments thereof. Furthermore, the DNA encoding the variable region of the antibody can be inserted into the DNA encoding other antibodies to produce chimeric antibodies (see, for example, U.S. Pat. No. 4,816,567). Single chain antibodies fall within the scope of the present invention.

Methods of producing polyclonal antibodies are known to those of skill in the art. Typically, an immunogen, preferably a purified protein, is mixed with an adjuvant and animals are immunized with the mixture. The animal's immune response to the immunogen preparation is monitored by taking test bleeds and determining the titer of reactivity to the PEDF variant or fragment of interest. When appropriately high titers of antibody to the immunogen are obtained, usually after repeated immunizations, blood is collected from the animal and antisera are prepared. Further fractionation of the antisera to enrich for antibodies reactive to the protein can be done if desired (see for example, Harlow and Lane (1988) Antibodies: A Laboratory Manual CSH Press, the content of which is incorporated by reference as if fully set forth herein).

Monoclonal antibodies can be obtained by various techniques familiar to those skilled in the art. Typically, spleen cells from an animal immunized with a desired antigen are immortalized, commonly by fusion with a myeloma cell (see, Kohler and Milstein (1976) Eur. J. Immunol. 6:511 519, incorporated herein by reference). Alternative methods of immortalization include transformation with Epstein Barr Virus, oncogenes, or retroviruses, or other methods known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according, e.g., to the general protocol outlined by Huse, et al. (1989) Science 246:1275 1281.

Other suitable techniques involve selection of libraries of antibodies in phage or similar vectors. See, e.g., Huse, et al. (1989) Science 246:1275 1281; and Ward, et al. (1989) Nature 341:544 546. The antibodies of the present invention may be used with or without modification. However, the antibodies can be labeled by joining, either covalently or non-covalently, a substance which provides for a detectable signal. A wide variety of labels and conjugation techniques are known and are reported extensively in both the scientific and patent literature. Suitable labels include radioactive agents, enzymes, substrates, cofactors, inhibitors, fluorescent moieties, chemiluminescent moieties, magnetic particles, and the like.

Pharmaceutical Compositions and Administration Routes

The present invention provides pharmaceutical compositions comprising a therapeutically effective amount of a PEDF variant, fragment, analog or fusion protein thereof having anti-angiogenic activity and a pharmaceutically acceptable carrier, the PEDF variant, fragment, analog or fusion protein thereof comprises a plurality of altered phosphorylation sites.

The pharmaceutical compositions of the present invention can be formulated as pharmaceutically acceptable salts of the proteins, polypeptides or peptides of the present invention. The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the protein, polypeptide or peptide of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

The term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic compound is administered. Such pharmaceutical carriers can be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, ethanol and the like. The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose are also envisioned.

The compositions can take the form of solutions, suspensions, emulsion, tablets, pills, capsules, powders, sustained-release formulations and the like. The composition can be formulated as a suppository, with traditional binders and carriers such as triglycerides, microcrystalline cellulose, gum tragacanth or gelatin. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of an anti-angiogenic PEDF variant or a fragment, analog or fusion protein thereof, preferably in a substantially purified form, together with a suitable amount of carrier so as to provide the form for proper administration to the subject.

The amount of the anti-angiogenic PEDF variant, a fragment, analog or fusion protein thereof which will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test bioassays or systems.

Depending on the location of the tissue of interest, the PEDF variant, analog or fragment thereof can be supplied in any manner suitable for the provision of the PEDF variant to endothelial cells within the tissue of interest. Thus, for example, a composition containing a source of PEDF variant (i.e., a PEDF variant polypeptide, or an isolated polynucleotide encoding a PEDF variant, or a PEDF variant expression vector, or cells expressing PEDF variant, as described herein above) can be introduced into the systemic circulation, which will distribute the source of PEDF to the tissue of interest. Alternatively, a composition containing a source of PEDF can be applied topically to the tissue of interest (e.g., injected, or pumped as a continuous infusion, or as a bolus within a tumor, applied to all or a portion of the surface of the skin, dropped onto the surface of the eye, etc.).

Methods of introduction of a pharmaceutical composition comprising a source of PEDF variant include, but are not limited to, topical, intradermal, intramuscular, intraperitoneal, intravenous, subcutaneous, intranasal, epidural, ophthalmic, and oral routes. The compounds may be administered by any convenient route, for example by infusion or bolus injection, by absorption through epithelial linings (e.g., oral mucosa, rectal and intestinal mucosa, etc.), and may be administered together with other therapeutically active agents. It is preferred that administration is localized, but it may be systemic. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir. Pulmonary administration can also be employed, e.g., by use of an inhaler or nebulizer, and formulation with an aerosolizing agent.

It may be desirable to administer the pharmaceutical composition of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, by means of a medical patch or by means of an implant, said implant being of a porous, non-porous, or gelatinous material. According to some preferred embodiments, administration can be by direct injection e.g., via a syringe, at the site of a tumor or neoplastic or pre-neoplastic tissue.

For topical application, an anti-angiogenic PEDF variant, analog or fragment thereof can be combined with a pharmaceutically acceptable carrier so that an effective dosage is delivered, based on the desired activity (i.e., ranging from an effective dosage, for example, of 1.0 pM to 1.0 mM to attenuate or prevent localized angiogenesis). The carrier may be in the form of, for example, and not by way of limitation, an ointment, cream, gel, paste, foam, aerosol, suppository, pad or gelled stick A topical composition for treatment of some of the eye disorders comprises an effective amount of an anti-angiogenic PEDF variant in a opthalmologically acceptable excipient such as buffered saline, mineral oil, vegetable oil such as corn or arachis oil, petroleum jelly, and Miglyol 182, alcohol solutions, or liposomes or liposome-like products. These compositions may also include preservatives, antioxidants, antibiotics, immunosuppressants, and other therapeutically effective agents, which do not exert a detrimental effect on the anti-angiogenic PEDF variant.

For directed internal topical applications, the pharmaceutical composition may be in the form of tablets or capsules, which can contain any of the following ingredients or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate or Sterotes; or a glidant such as colloidal silicon dioxide. When the dosage unit form is a capsule, it can contain, in addition to materials of the above type, a liquid carrier such as fatty oil. In addition, dosage unit forms can contain various other materials which modify the physical form of the dosage unit, for example, coatings of sugar, shellac, or other enteric agents.

An anti-angiogenic PEDF variant, a fragment or analog thereof can be delivered in a controlled release system. In one embodiment, an infusion pump may be used to administer an anti-angiogenic PEDF variant, a fragment or analog thereof, such as for example, that is used for delivering insulin or chemotherapy to specific organs or tumors. In a preferred form, an anti-angiogenic PEDF variant, analog or fragment thereof is administered in combination with a biodegradable, biocompatible polymeric implant, which releases the anti-angiogenic PEDF variant over a controlled period of time at a selected site. Examples of preferred polymeric materials include polyanhydrides, polyorthoesters, polyglycolic acid, polylactic acid, polyethylene vinyl acetate, copolymers and blends thereof (See, Medical applications of controlled release, Langer and Wise (eds.), 1974, CRC Pres., Boca Raton, Fla.). In yet another embodiment, a controlled release system can be placed in proximity of the therapeutic target, thus requiring only a fraction of the systemic dose.

Uses of PEDF Variants

The present invention provides a method for treating diseases or disorders, particularly diseases or disorders associated with neovascularization. The method of treatment comprises administering to a patient in need thereof a pharmaceutical composition comprising as an active ingredient a therapeutically effective amount of a PEDF source and a pharmaceutically acceptable carrier. The PEDF source according to the present invention includes a PEDF variant polypeptide, i.e., an anti-angiogenic PEDF variant, fragment, analog, or fusion protein thereof; an isolated polynucleotide sequence encoding a PEDF polypeptide variant of the invention; an expression vector comprising the isolated polynucleotide sequence encoding the PEDF polypeptide variant of the invention; and a host cell transfected with an expression vector comprising an isolated polynucleotide sequence encoding the PEDF polypeptide variant of the invention.

The inhibition of angiogenesis is generally considered to be the halting of the development of new blood vessels, whether they develop by sprouting or by the arrival and subsequent differentiation into endothelial cells of circulating stem cells. However, since PEDF has been shown to induce apoptosis of activated endothelial cells, inhibition of angiogenesis in the context of the present invention should also be construed to include the killing of cells by a PEDF variant, particularly cells in existing vessels near or within a tumor. Thus, within the context of the present invention, inhibition of angiogenesis includes inhibition of the development of new blood vessels, which inhibition may or may not be accompanied by the destruction of nearby existing vessels. The terms "neovascularization" and angiogenesis are used interchangeably throughout the specification and claims.

A "therapeutic" treatment is a treatment administered to a subject who exhibits signs of pathology for the purpose of diminishing or eliminating those signs.

A "therapeutically effective amount" of a PEDF source is that amount of PEDF source which is sufficient to provide a beneficial effect to the subject to which the PEDF source is administered.

Patients in need thereof may suffer from one or more disease or disorder associated with neovascularization or may have been determined to have a greater susceptibility to a disease or disorder associated with neovascularization. Thus, the method of treatment according to the present invention includes both therapeutic and prophylactic utility.

Neovascular disease that can be treated with an anti-angiogenic PEDF source is cancer including, but not limited to, solid tumors such as sarcoma, carcinoma, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor leiomydsarcoma, rhabdomyosarcoma, colon carcinoma, pancreatic cancer, breast cancer, ovarian cancer, prostate cancer, squamous cell carcinoma, basal cell carcinoma, adenocarcinoma sweat gland carcinoma, sebaceous gland carcinoma, papillary carcinoma, papillary adenocarcinoma, cystadenocarcinoma, medullary carcinoma, bronchogenic carcinoma, renal cell carcinoma, hepatoma bile duct carcinoma, choriocarcinoma, seminoma, embryonal carcinoma, Wilms' tumor cervical cancer, testicular tumor, lung carcinoma, small cell lung carcinoma, bladder carcinoma, epithelial carcinoma, glioma, astrocytoma, medulloblastoma, craniopharyngioma, ependymoma, Kaposi's sarcoma, pinealoma, hemangioblastoma, acoustic neuroma, oligodendroglioma, menangioma, melanoma, neuroblastoma, and retinoblastoma.

Ocular disorders associated with neovascularization which can be treated with an anti-angiogenic PEDF source include, but are not limited to, neovascular glaucoma, diabetic retinopathy, retinoblastoma, retrolental fibroplasias, uveitis, retinopathy of prematurity, macular degeneration, corneal graft neovascularization, eye inflammatory diseases, ocular tumors such as retinal tumors and choroidal tumors, and diseases associated with retinal, choroidal or iris neovascularization.

Other disorders, which can be treated with an anti-angiogenic PEDF source include, but are not limited to, hemangioma, arthritis, psoriasis, angiofibroma, atherosclerotic plaques, hemophilic joints, and hypertrophic scars.

An anti-angiogenic PEDF variant can be tested in vivo for the desired therapeutic or prophylactic activity as well as for determination of a therapeutically effective dosage. For example, a PEDF source can be tested in suitable animal model systems prior to testing in humans, including, but not limited to, rats, mice, chicken, cows, monkeys, rabbits, and the like. For in vivo testing, prior to administration to humans, any animal model system known in the art can be used (see examples herein below).

According to another aspect, the present invention provides a method for treating a neurodegenerative disease or condition in a subject comprising administering to the subject in need thereof a therapeutically effective amount of a pharmaceutical composition according to the principles of the invention and a pharmaceutically acceptable carrier.

"Neurotrophic" activity is defined herein as the ability to induce differentiation to a neuronal cell population. For example, PEDF's ability to induce differentiation in cultured retinoblastoma cells is considered neurotrophic activity. Neurotrophic activity also includes neuronotrophic activity and gliastatic activity. "Neuronotrophic" activity is defined herein as the ability to enhance survival of neuronal cell populations. "Gliastatic" activity is defined herein as the ability to inhibit glial cell growth and proliferation.

Many neurodegenerative diseases and other insults to the CNS (brain and retina) are typified by death of neurons and overpopulation by glia (gliosis). PEDF can be used effectively in these conditions to prolong the life and functioning of the primary neurons and to stave off the glial advance. PEDF source can be effective, for example, in blocking microglial activation in response to CNS injury as well as prolonging/sparing the lives of neurons. In the retina, it is predictable that PEDF inhibits the Muller glial cells. Since Muller cells are similar to astroglia, a PEDF source would be similarly effective in blocking gliosis in conditions such as retinal detachment, diabetes, Retinitis Pigmentosa, and the like as well as sparing the lives of the retinal neurons.

It is thought that transplantation of neurons can cure certain pathologies. For example, in Parkinson's disease, transplantation of specific fetal brain cells into patients could alleviate or cure the problems associated with the disease. One of the major problems to contend with, though, would be to prolong the life of the transplanted cells and to keep them differentiated, e.g., secreting the proper substances. Pretreatment of the cells with a PEDF variant could aid in both of these areas. Similarly, transfection of either neurons or astroglia with a vector comprising an isolated polynucleotide encoding a PEDF variant before implantation can be a long-term source of a PEDF variant at the transplantation site.

There is much activity in attempts at transplantation of neural retina and photoreceptor cells to help cure blindness. Attempts to date have not been fruitful both due to non-differentiation and death of the grafts. A PEDF source may help in both regards. Specifically, photoreceptor neurons to be transplanted can be pretreated with a PEDF source before surgery. Alternatively, a vector comprising an isolated polynucleotide encoding a PEDF variant can be transfected at high levels into adjacent retinal pigment epithelial (RPE) cells where they can serve as a supranormal source of the protein. Several investigators have now shown that cultured RPE cells survive very well after transplantation into the interphotoreceptor space of test animals. Transfection of human RPE cells in vitro with an isolated polynucleotide encoding a PEDF gene enable the use of these cells in retinal transplantation.

Where PEDF is produced naturally, it can be present in concentrations as high as about 250 nM. Because PEDF variants are non-toxic, they can be supplied to tissues in a far more concentrated dosage. However, given PEDF variant's potency, it can be employed at far reduced concentrations, such as about 10 nM or less (e.g., as little as 0.01 nM). Depending on the formulation of a composition comprising the PEDF source, it is supplied over a time course sufficient to retard angiogenesis and/or to induce neurotrophic activity within a desired tissue.

In some protocols, repeated application may enhance the anti-angiogenic activity and/or the neurotrophic activity of the PEDF variant and may be required in some applications. Where the source of PEDF is a PEDF expression vector, the cells expressing a PEDF variant may produce an effective amount of the PEDF variant (i.e., sufficient to exert one or more of the biological activities of PEDF).

PEDF variants can be administered alone or in conjunction with other therapeutic modalities. It is appropriate to administer a PEDF variant as part of a treatment regimen involving other therapies, such as surgery, drug therapy, photodynamic therapy, and/or radiation therapy.

EXAMPLES

Materials and Methods

Reagents and Antibodies

Recombinant human CK2 (expressed in *E. coli*) was purchased from Calbiochem (Darmstadt, Germany). The catalytic subunit of PKA was purified as described (Beavo J. A., et al. Methods in Enzymol. 38C: 299-308, 1974). Endothelial mitogen (ECGS) was purchased from Biomedical Technologies Inc. (Stoughton, Mass., USA). Recombinant human bFGF (expressed in *E. coli*), Poly-L-lysine (70-150 kDa) and porcine intestinal heparin were purchased from Sigma (St. Louis, Mich.). Matrigel was purchased from BD Biosciences (MA, USA). Restriction enzymes were purchased from Roche (Manhemin, Germany). Pfu DNA polymerase was purchased from Promega (WI, USA). Polyclonal antibodies against PEDF were prepared by the Antibody Unit of the Weizmann Institute of Science. Full-length human PEDF cDNA was provided by Dr. N. Bouck (Northwestern University, Chicago, Ill., USA).

Cell Cultures

Human Y-79 retinoblastoma cells were grown in MEM supplemented with 2 mM L-Glutamine and 15% fetal calf serum. HEK-293T cells were cultured in DMEM F-12 supplemented with 10% FCS. HUVEC were grown in M-199 supplemented with 20% FCS, 25 μg/ml ECGS mitogen, and 5 U/ml heparin.

Construction of Recombinant PEDF (rPEDF) Variants

The triple variants were generated by replacing a Hind III and Kpn I digestion fragment (1-362 bp), containing the region of Ser24 and Ser114 and their mutations (Maik-Rachline, G., et al. Blood: 299-308, 2005 and WO 2006/054278, the content of which is incorporated by reference), with the same fragment in plasmids containing various mutations in Ser227. This yielded the triple variants as follows:

EEE variant, S24,114E insert ligated with digested pcDNA3-S227E vector.

AAE variant, S24,114A insert ligated with digested pcDNA3-S227E vector.

AAA variant, S24,114A insert ligated with digested pcDNA3-S227A vector.

EEA variant, S24,114E insert ligated with digested pcDNA3-S227A vector.

Production of rPEDF

The various plasmids carrying rPEDF or the variants were introduced into HEK-293T cells using the LipofectAMINE reagent, and the secreted proteins were purified on $Ni^{+2}$ columns as described (Maik-Rachline, G., et al. Blood: 299-308, 2005).

The designation and the SEQ ID NOs of the amino acid and nucleotide sequences of the various PEDFs disclosed herein are as follows:

| Amino acid substitution | Designation | Amino acid SEQ ID NO: | Nucleotide SEQ ID NO: |
|---|---|---|---|
| None | rPEDF or plPEDF | 1 | 6 |
| S24,114, 227E | EEE | 2 | 7 |
| S24,114A, 227E | AAE | 3 | 8 |
| S24,114, 227A | AAA | 4 | 9 |
| S24,114E, 227A | EEA | 5 | 10 |
| S24E | S24E | 11 | |
| S24,114E | S24,114E | 12 | |
| S227E | S227E | 13 | |
| S114E | S114E | 14 | |

Purification of PEDF from Human Plasma plPEDF was purified from human citrated plasma (1 L) by a 9-20% PEG cut followed by DEAE-Sephacel column (2.9×40 cm) and heparin agarose column as previously described (Maik-Rachline, G., et al. Blood: 299-308, 2005).

In Vitro Phosphorylation of PEDF

The phosphorylation assay (40 μl) contained either rPEDF, plPEDF or rPEDF variants (50 μg/ml). For CK2: the constituents were CK2 (4 μg/ml), glycerol (2%), NaCl (20 mM), β-mercaptoethanol (0.1 mM), $MgCl_2$ (20 mM), [$\gamma^{32}P$]-ATP (10 μM), poly-L-lysine (200 nM), and Tris-HCl (50 mM pH 7.4). For PKA: pure catalytic subunit of PKA (2.5 μg/ml), $MgCl_2$ (10 mM), heparin (50 μg/ml), [$\gamma^{32}P$]-ATP (10 μM), and Tris-HCl (50 mM pH 6.5). Reactions were continued for 45 min at 30° C. Then, boiled sample buffer was added, and the samples were subjected to 10% SDS-PAGE.

Determination of ERK Phosphorylation

Serum starved HUVEC were treated with the various rPEDF variants (10 nM) for 15 min. Following stimulation, the cells were harvested, the proteins were separated by SDS-PAGE, and phospho ERK and general ERK were detected by Western blotting using the appropriate antibodies as described (Aebersold, D. M., et al. Mol. Cell. Biol. 24:10,000-10,015, 2004).

Endothelial Cell Proliferation Assay

Proliferation was determined by the methylene blue assay as previously described (Oliver, M. H., et al., J. Cell Sci. 92: 513-518, 1989). Briefly, HUVEC were seeded in gelatin coated 24 well tissue culture plates ($20\times10^3$ cells/well) in M-199 supplemented with 2.5% FCS (0.5 ml/well). The various PEDFs were added immediately following seeding at quadraplicates (all at 10 nM) and plates were incubated at a humidified incubator for 48 hrs. Then cells were fixed in 4% buffered formaldehyde solution for 2 hrs, washed twice with 0.1 M sodium borate buffer, pH 8.5, and stained with 1% methylene blue dissolved in 0.1 M borate buffer solution for 20 min. Excess dye was washed out and cell-bound dye was eluted with 200 μl/well of 0.1 M HCl. The optical density value was read at 595 nm in Wallac 1420 multilabel counter. The data was analyzed in Microsoft Excel, using cell proliferation in 2.5% FCS medium as a control.

Neurite Outgrowth Assay

Human Y-79 retinoblastoma cells (obtained from ATCC) were assayed for neurite outgrowth as previously described (Becerra, S. P., et al., J. Biol. Chem. 268: 23148-23156, 1993). One ml of a Y-79 cell suspension ($2.5\times10^5$ cells/ml) were incubated with rPEDF, or the various rPEDF variants (20 nM) in MEM supplemented with 2 mM L-glutamine, antibiotics, and 0.1% ITS. After 7 days in culture the cells were transferred to poly-D-lysine coated plates, and their neurite outgrowth was monitored by light microscopy at various periods of time.

In Vivo Matrigel Plug Angiogenesis Assay

Matrigel (0.5 ml/mouse) kept on ice was mixed with bFGF at the indicated concentration with or without PEDF (20 nM), and was injected subcutaneously into the flank of 8 week old nude mice as described (Passaniti, A., et al., Lab. Invest. 67: 519-528, 1992). After injection the Matrigel rapidly formed a plug. On day 7, mice were sacrificed and their skin was carefully pulled back to expose the intact plugs. The plugs were removed, fixed (4% formaldehyde), paraffin embedded and sectioned. Sections were stained using Hematoxilin-Eosin (H&E). Endothelial cells/microvessels infiltrating the Matrigel were confirmed by Masson's Trichrome staining.

Example 1

The CK2 Phosphorylation Mutant of PEDF is not a PKA Substrate

The interplay between CK2 and PKA phosphorylations has been studied. As a first step, it was examined whether each phosphorylation changes the ability of PEDF to serve as a substrate for the other protein kinase. To this end, the negative charge of phosphorylated serine was mimicked by replacing it with the negatively charged glutamic acid residue, while the non-phosphorylated state of serine was mimicked by alanine, which cannot serve as a phosphor-acceptor. Thus, the CK2 phosphorylation variant S24,114E (EE) was subjected to PKA phosphorylation by incubating it with the pure catalytic subunit of PKA and [$\gamma^{32}$P]-ATP. Since PKA phosphorylation is often pH-dependent, the experiment was performed at different pHs.

As shown in FIG. 1A, while rPEDF served as a good substrate to PKA, the phosphorylated variant, S24,114E, was not phosphorylated by PKA under the conditions used (FIG. 1A). However, a brief heat treatment, which was designed to mildly abrogate the native structure of the S24,114E variant, restored its phosphorylation by PKA (FIG. 1B). This result indicates that the lack of phosphorylation is due to a conformation-dependent masking of the PKA phosphorylation site by the phosphorylated CK2 sites, and this is despite the fact that the two sites are located in separate regions of the PEDF molecule. Furthermore, the variant S24,114A (AA), which can not be phosphorylated by CK2 at all, was readily phosphorylated by PKA under the different reaction conditions tested (FIG. 1C) indicating that the lack of phosphorylation is indeed due to the negative charge on Ser 24 and Ser114. In contrast to the prevention of PKA phosphorylation by the negative charges at the CK2 sites, negative charge at the PKA site (Ser227) had no significant effect on CK2 phosphorylation. This was true for both PKA phosphorylatable and non-phosphorylatable site variants (S227E and S227A, respectively), which were both readily phosphorylated by CK2 (FIG. 1D). The hyperphosphorylation of the denatured PEDF by CK2 was previously reported (Maik-Rachline, G. et al. ibid), and indicate that additional CK2 sites are exposed by PEDF denaturation. Moreover, as previously shown, the phosphorylation of the plPEDF by CK2 was significantly lower than CK2 phosphorylation of the rPEDF (FIG. 1D), and this probably occurs due to pre-phosphorylation of the circulating protein on these sites. Thus, CK2 phosphorylation of Ser24 and Ser114 induces a conformational change in PEDF that makes Ser227 inaccessible to PKA phosphorylation. However, PKA phosphorylation of Ser227 does not affect the ability of PEDF to be phosphorylated by CK2.

Example 2

Characterization of the Triple Variants of PEDF

The inventors of the present invention have previously shown that PEDF purified from the circulating blood (plPEDF) contains phosphates on its CK2 sites and to a lesser extent also on its PKA site (Maik-Rachline, G. et al. ibid; and FIG. 1 herein above). In addition, the results herein above show that the three PEDF sites can be phosphorylated at the same time, first by PKA and then by CK2 (FIG. 1). In view of these findings, it became important to characterize the effects of the simultaneous phosphorylation of PEDF by both these kinases. Therefore, a set of triple site variants was constructed by replacing the CK2 and PKA phosphorylation sites, Ser 24, 114 and 227, with Ala or Glu as follows: S24E114E227E (EEE) mimics phosphorylation on the CK2 and PKA sites, S24E114E227A (EEA) mimics phosphorylation on CK2 but not PKA sites, S24A114A227E (AAE) mimics phosphorylation on PKA but not CK2 sites, and S24A114A227A (AAA) mimics the non CK2 or PKA phosphorylated PEDF (FIG. 2A). The use of the Glu mutants, rather than the partially phosphorylated plPEDF was important because it provides a homogenous population of molecules with a negative charge in the relevant sites, and thereby enable the accurate detection of the phosphorylation effect. The mutations of the phosphorylated Ser to Ala residues were important as well, because they enable obtaining a homogenous population of non-phosphorylated molecules. This is unlike the small amount of phosphorylation that occurs on the PKA site in the S24,114E or S24,114A, as well as on the CK2 site in the S227E and S227A mutants (Maik-Rachline, G., et al., ibid), which can partially affect the properties of these molecules. These variants were expressed by transfecting HEK 293T cells with the full-length human PEDF cDNA or the variants, and purified on a $Ni^{+2}$ column.

To characterize the variants and confirm their biochemical integrity, each of them was subjected to an in vitro phosphorylation by CK2 or PKA. The AAE and the AAA variants almost completely abolished CK2 phosphorylation (FIG. 2B). On the other hand, the triple mutants EEE and EEA were readily phosphorylated by CK2, indicating that these mutants expose additional phosphorylation sites in accordance with the hyperphosphorylation of the previously described S24, 114E (EE) mutant (Maik-Rachline, G., et al., ibid). Therefore, the addition of the mutations of S227A or S227E to the CK2 mutated sites did not significantly affect their CK2 phosphorylation level as compared to the phosphorylation of S24, 114E alone (FIG. 2B). In addition, none of the triple mutants was phosphorylated by PKA (FIG. 2C), indicating that mutation of the CK2 sites either to Glu or to Ala within the triple mutants did not affect the conformational structure of the PKA site.

Example 3

The Effect of PEDF Variants on ERK Activation

Although the receptor for PEDF has not yet been identified, it was shown that this factor can stimulate various intracellular signaling processes including the extracellular signal-regulated kinase (ERK)/mitogen-activated protein kinase (MAPK) cascade. To further characterize the various triple variants of PEDF, their effect on ERK activation in HUVEC was examined. Thus, the various variants were added to serum-starved HUVEC and the activity of ERK was determined using anti phospho-ERK and anti general ERK antibodies.

Figure 3B:
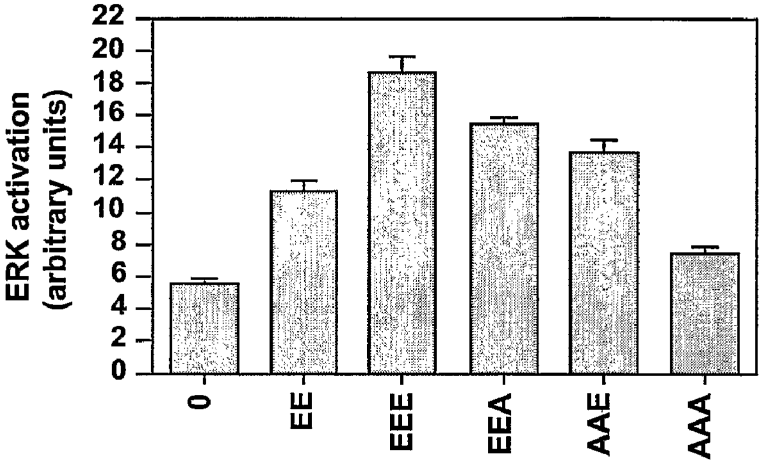

In their previous study, the present inventors showed that phosphorylation of PEDF by CK2 markedly elevated the effect of rPEDF on ERK activation, while PKA phosphorylation alone had essentially no effect (Maik-Rachline, G., et al. ibid). The present findings show that the S24,114E variant induced a significant ERK phosphorylation (FIGS. 3A and 3B), which was higher than the phosphorylation induced by rPEDF. However, the phosphorylation of ERK induced by the triple phosphorylation variant EEE resulted in an even stronger phosphorylation, which was about 1.5 fold higher than that of the S24,114E variant (FIG. 3A-B). The EEA and the AAE variants induced ERK phosphorylation to a slightly higher level than the S24,114E variant, while the AAA variant significantly reduced the ability of PEDF to activate ERK. These results indicated that phosphorylation of PEDF by either PKA or CK2 is necessary for the PEDF-induced activation of the ERK cascade and that accumulative phosphorylation of the three sites of these kinases significantly elevates this induction.

Example 4

The Effect of PEDF Variants on Cell Proliferation

Figure 3C:
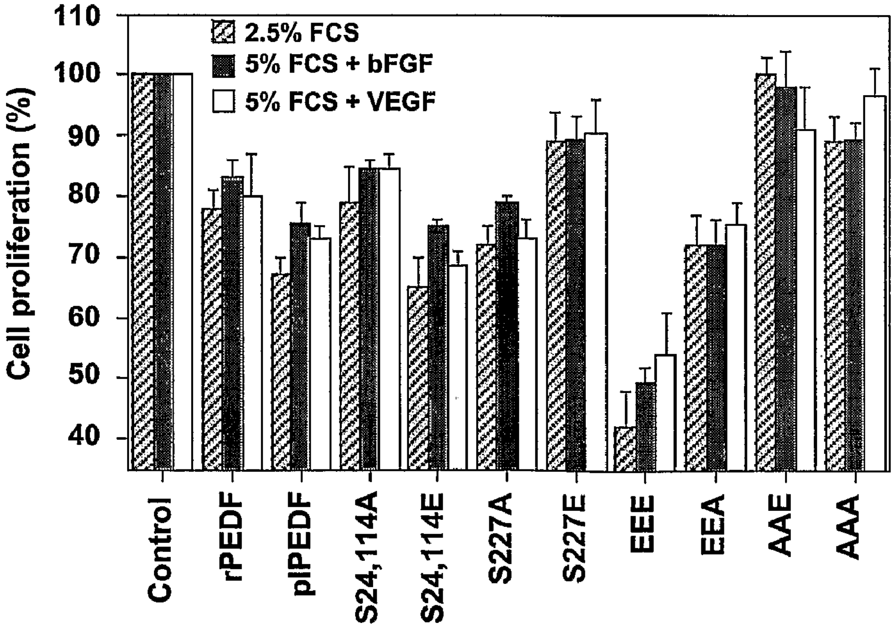

PEDF was previously shown to inhibit cell proliferation of endometrial carcinoma cells, and to induce apoptosis of endothelial cells. The aim of this experiment was to determine the effect of PEDF and its phosphorylated variants on HUVEC proliferation. To this end, HUVEC were seeded in a 24 well tissue culture plate, maintained in a medium supplemented with 2.5% FCS with or without various PEDFs for 48 hrs, and then analyzed for proliferation rate by the methylene blue assay (Oliver, M. H., et al. J. Cell Sci. 92:513-518, 1989). Under these conditions, rPEDF inhibited HUVEC proliferation to a moderate extent (22%, FIG. 3C), while the inhibitory effect of PEDF purified from plasma (plPEDF) was more pronounced (33%). The inhibition on HUVEC proliferation observed when cells were treated with the S24,114E, variant was very similar to the inhibition observed by plPEDF, indicating again that PEDF in the circulating plasma is largely phosphorylated on its CK2 sites (see above). Interestingly, when cells were treated with the EEE variant, the level of inhibition was highly elevated (57%), whereas cells treated with the EEA variant behaved very similarly to cells treated with the S24,114E variant (27% and 33% inhibition, respectively). On the other hand, the PKA phosphorylation variants, S227E and AAE, had almost no effect on HUVEC proliferation. In addition, cells treated with the non-phosphorylated variants, S24,114A and S227A showed similar levels of proliferation as cells treated with rPEDF, whereas the AAA mutant had only a small effect on HUVEC proliferation. Thus, these results show that the inhibition of HUVEC proliferation is dependent on the phosphorylation state of PEDF. In particular, cell proliferation is inhibited by PEDF phosphorylated on its CK2 sites, and this inhibition is highly increased upon addition of a negative charge in the PKA site to that of the CK2 sites.

Example 5

The Effect of the Triple Mutations on PEDF-Induced Neurotrophic Activity

Figure 4A:
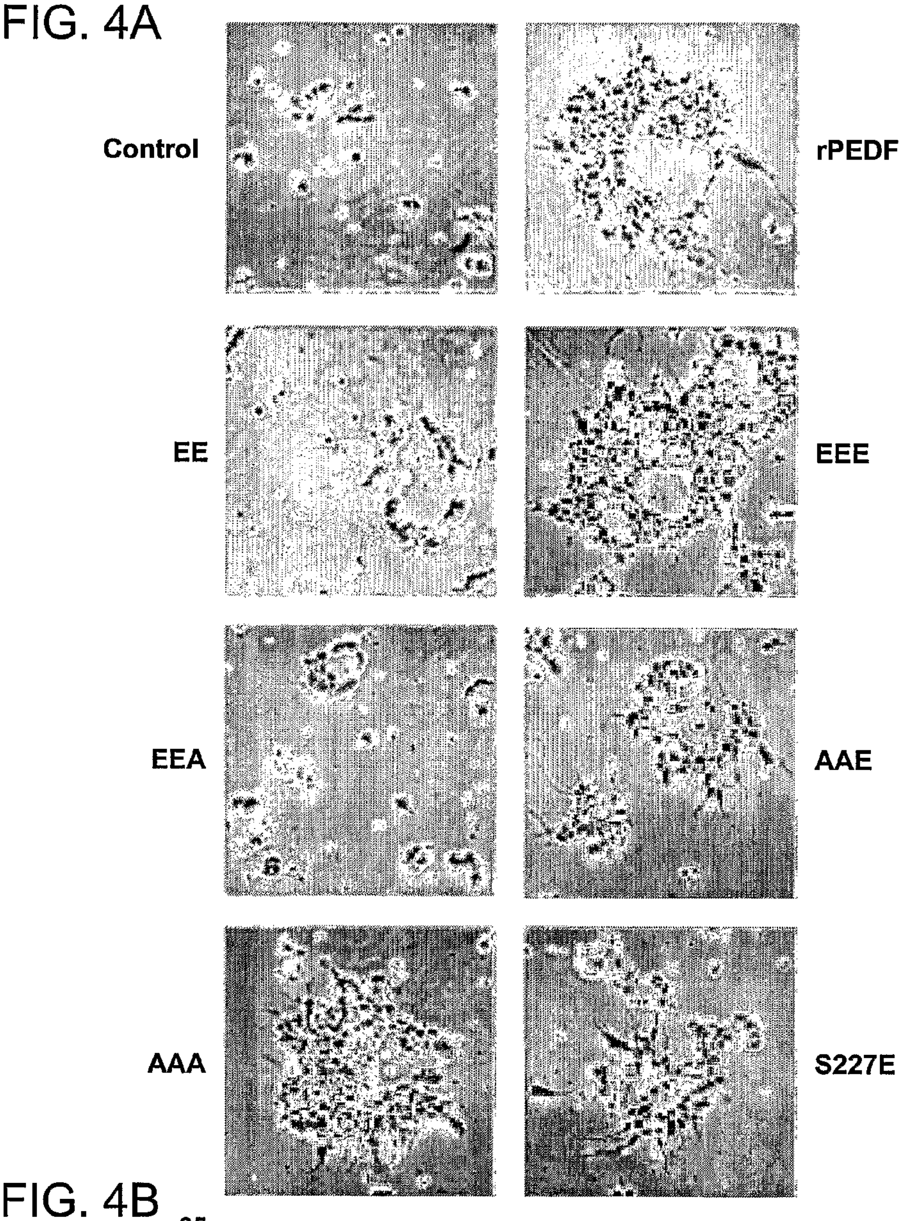
FIGS. 4A-B show the effect of rPEDF and its variants on PEDF-induced neurotrophic activity.
Figure 4B:
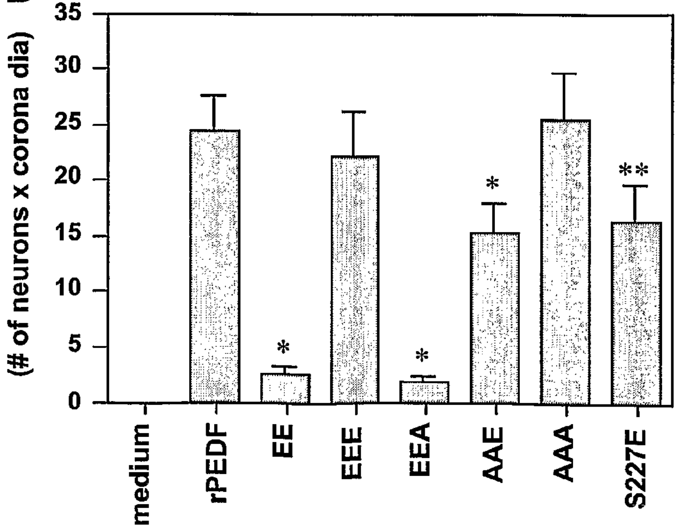

The present inventors previously showed that CK2 phosphorylation significantly reduces the neurotrophic effect of PEDF, while PKA phosphorylation of PEDF has no, or very little, influence on the neurotrophic effect of PEDF (Maik-Rachline, G., et al. ibid). The present study was aimed at examining whether simultaneous phosphate incorporation to the PKA and CK2 sites of PEDF modulate the ability of the PEDF variant to induce differentiation in human retinoblastoma Y-79 cells in culture. Surprisingly, cells treated with the EEE variant (FIG. 4) exhibited neurite outgrowth and formed large aggregates, while the EEA variant induced the formation of small corona-like structures, which were very compact, without any sprouts projecting from these cells, in a similar fashion to cells treated with the S24,114E variant. Treating Y-79 cells with PKA phosphorylation site variants: the S227E and AAE, resulted in a different cell phenotype, where colonies were smaller, although their processes were clearly observed. These findings indicate that while CK2 phosphorylation significantly reduces PEDF neurotrophic effect, the addition of phosphate to the PKA site, on top of the phosphorylation by CK2, preserves the neurotrophic activity of PEDF. This occurs despite the minimal effect of PEDF phosphorylated on its PKA site alone.

Example 6

The Effect of the Triple Amino Acid Substitution on the PEDF-Induced Anti-Angiogenic Activity In Vivo To further explore the effect of both CK2 and PKA phosphorylations on PEDF function, the influence of the triple variants on the anti-angiogenic activity of PEDF using the Matrigel plug assay was determined.

Figure 5A:
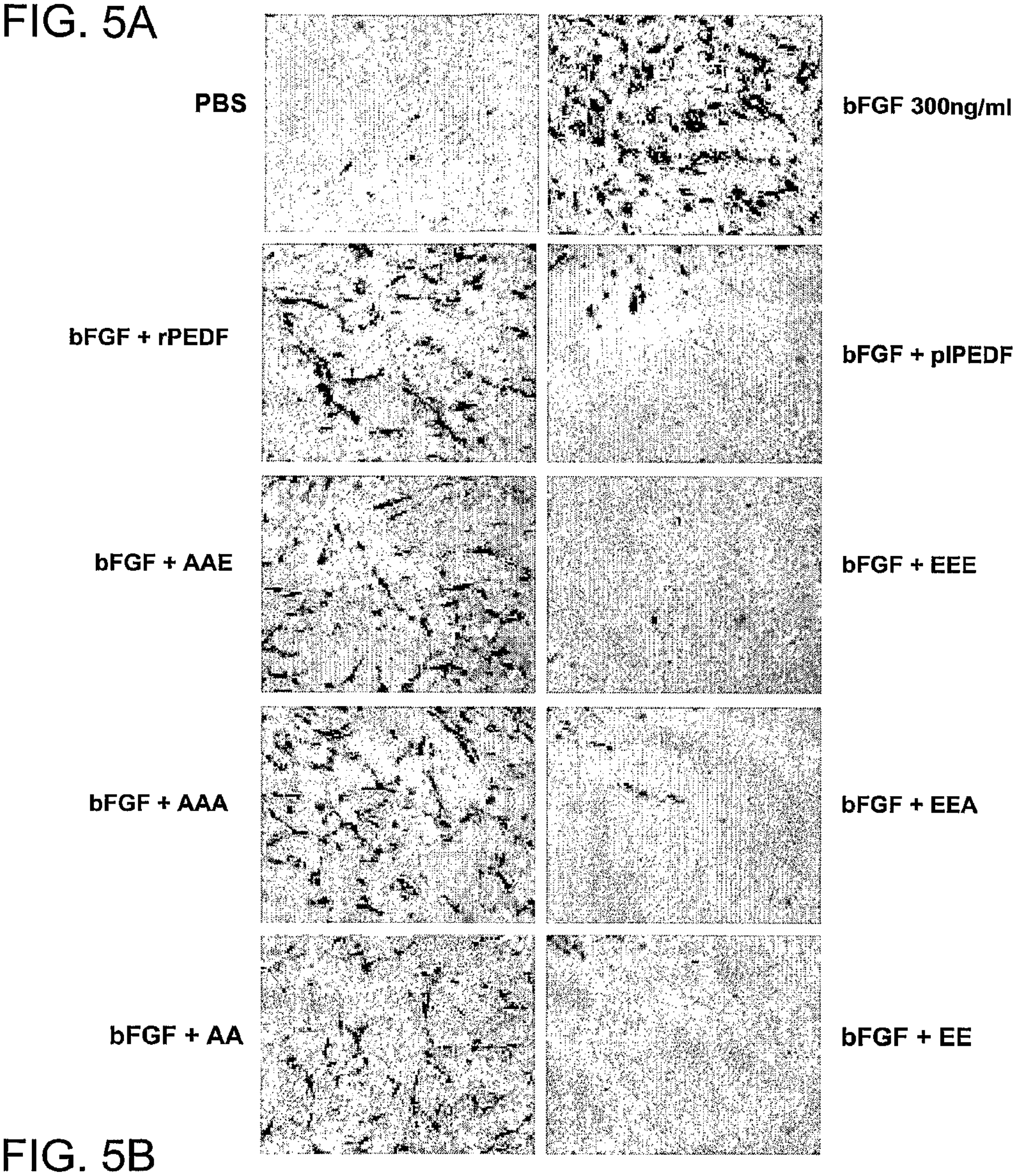
FIGS. 5A-B show the anti-angiogenic activity of the PEDF variants on a moderate bFGF-induced neovascularization.
Figure 5B:
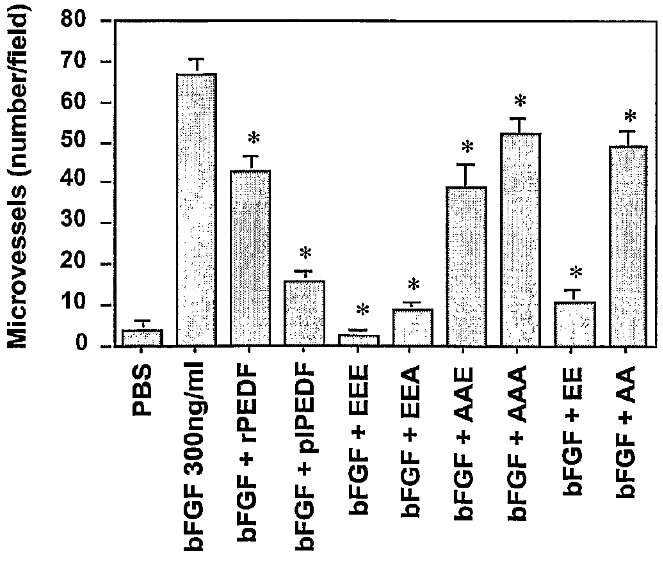

Liquid Matrigel supplemented with the examined factors was injected subcutaneously into CD-1 nude mice. The Matrigel polymerized to form a plug, which was removed after a week and analyzed for the growth and infiltration of blood vessels by histology staining. Matrigel plugs were treated with rPEDF, plPEDF or the various variants in combination with bFGF (300 ng/ml). As expected, control plugs treated with PBS showed a very minute angiogenic response, bFGF-treated plugs showed robust angiogenic activity, and the rPEDF, plPEDF as well as the S24,114E and S24,114A mutants exhibited the previously described anti-angiogenic activity in the system (FIG. 5, also Maik-Rachline, G., et al. ibid). The triple variants EEE or EEA reduced bFGF-induced angiogenesis to a degree that was roughly similar to the effect of S24,114E, while the AAA and AAE variants had only a minor effect that was roughly similar to that of S24,114A. Interestingly, the anti-angiogenic effect of the EEE variant, was somewhat higher than that of the other variants, but this was not statistically significant under the conditions used in the current experiment. It is noteworthy to mention that a few proliferating cells that did not form vessels were observed in the periphery of all plagues, independent of the type of the PEDF variant, suggesting that the anti-angiogenic activity is mediated in part by mechanisms that do not involve inhibition of proliferation.

Figure 6A:
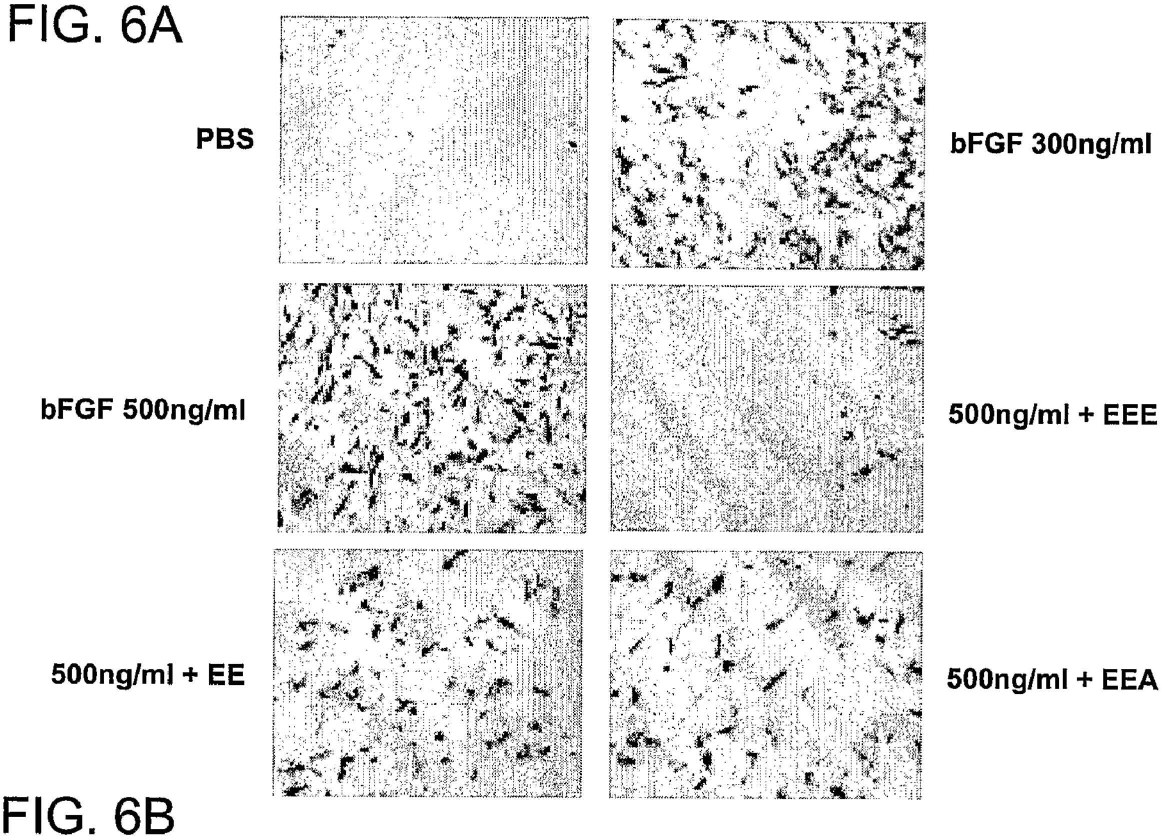
FIGS. 6A-B show the anti-angiogenic activity of the PEDF variants on an extensive bFGF-induced neovascularization.
Figure 6B:
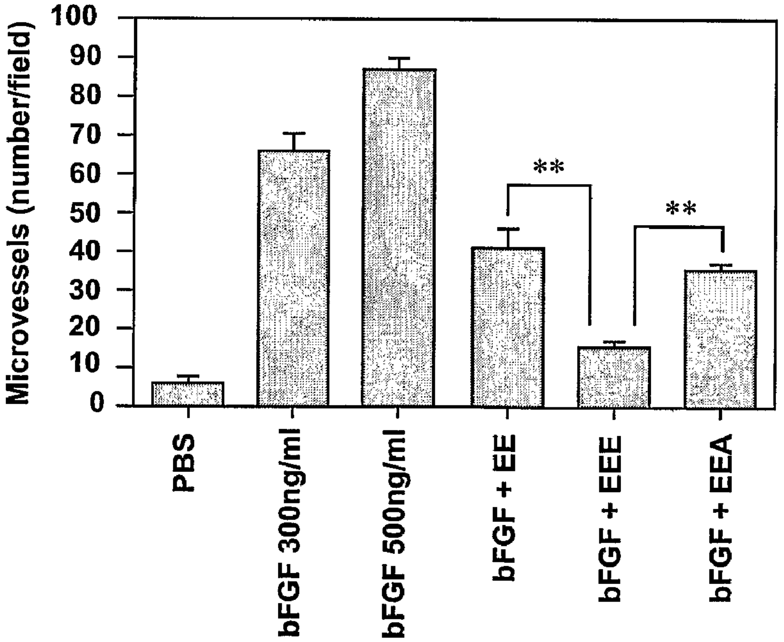

In view of the slightly better inhibition of blood vessel sprouting by the EEE variant, the possibility that this variant is indeed a better anti-angiogenic factor than the other phosphorylation variants was then examined. To this end, the inhibitory effect of these variants on Matrigel plugs treated with a higher level of bFGF (500 ng/ml) was determined. Overall, plugs that were treated with 500 ng/ml bFGF exhibited a higher angiogenic response than plugs treated with 300 ng/ml (FIG. 6). This was evident by a significant elevation in the number of cells infiltrating the plug (FIG. 6), and the clear staining of actual vessels in these plugs, which were not apparent in plugs treated with the lower concentration of bFGF. Under these higher bFGF levels, the EEE variant significantly increased PEDF anti-angiogenic activity, as no vessels were observed in the plug (FIG. 6). This inhibitory activity was significantly more pronounced as compared to the anti-angiogenic activity observed by the S24,114E or EEA mutants ($p=0.04$ and $p=0.01$, respectively). Therefore, these results indicate that PKA phosphorylation of PEDF is essential for its robust anti-angiogenic activity when combined with CK2 phosphorylation, but not when presented by itself. These results further indicate that the simultaneous phosphorylation of PEDF by CK2 and PKA results in a PEDF variant having the highest level of anti-angiogenic activity, more than the anti-angiogenic activity exhibited by the PEDF variant phosphorylated by CK2 alone.

Figure 7:
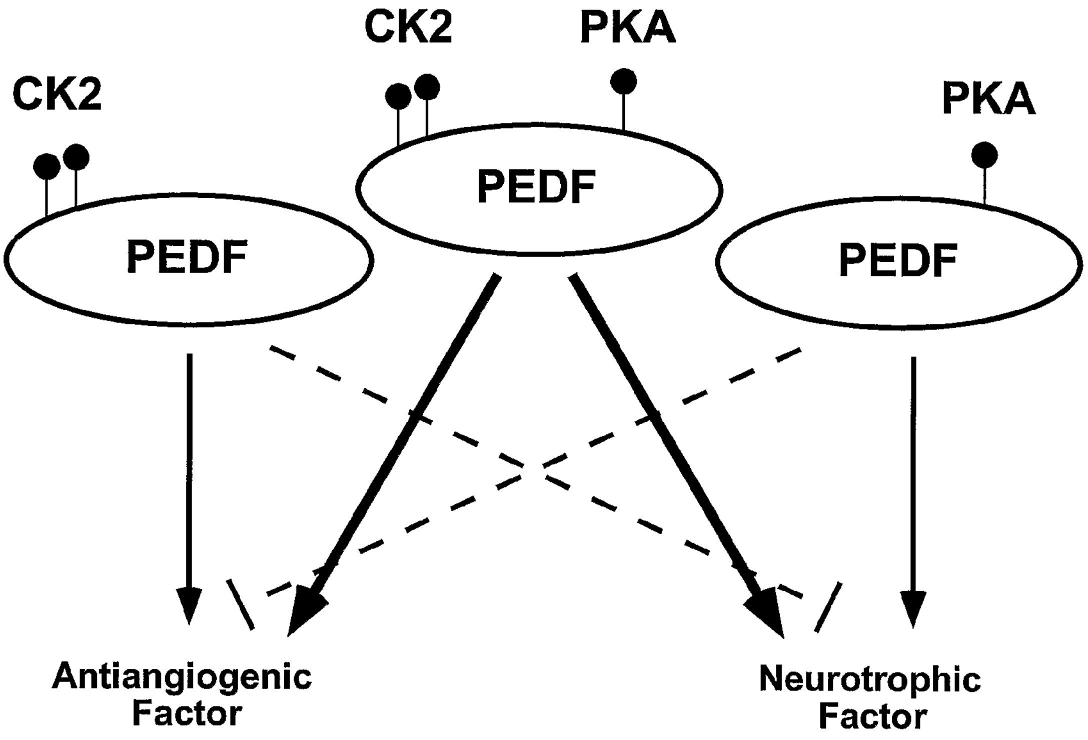
FIG. 7 shows a schematic presentation of the differential phosphorylation states of PEDF and their effect on PEDF function.

Thus, phosphorylation of PEDF plays an important role in the determination of its physiological activity. In the previous study of the present inventors (Maik-Rachline, G., et al. ibid), it was shown that extracellular phosphorylation of PEDF by CK2 abolishes PEDF neurotrophic activity, but enhances its anti-angiogenic activity, while PKA phosphorylation reduces PEDF anti-angiogenic activity without affecting its neurotrophic activity. In the present invention it is shown that combined replacement of the Ser at the PKA and CK2 phosphorylation sites to Glu turns PEDF to its most potent anti-angiogenic form, while retaining its neurotrophic activity. Considering all these observations, it can be concluded that the extracellular phosphorylation of PEDF by PKA, CK2, or both kinases together can modulate PEDF activities. Thus, the non-phosphorylated protein has weak anti-angiogenic as well as neurotrophic activities; the PKA-phosphorylated protein exhibits strong neurotrophic activity but not anti-angiogenic activity; the PEDF phosphorylated on the two CK2 sites exhibits anti-angiogenic activity without having any neurotrophic effect; and finally, the triply phosphorylated protein regains both activities. Furthermore, the anti-angiogenic activity of the triply phosphorylated protein is much higher than that of the non-phosphorylated or mono PKA phosphorylated-PEDF, and is also higher than that of the doubly CK2 phosphorylated protein (FIG. 7).

Example 7

The EEE Triple Variant Inhibits Growth of DU145 Tumor Xenograft

Figure 8A:
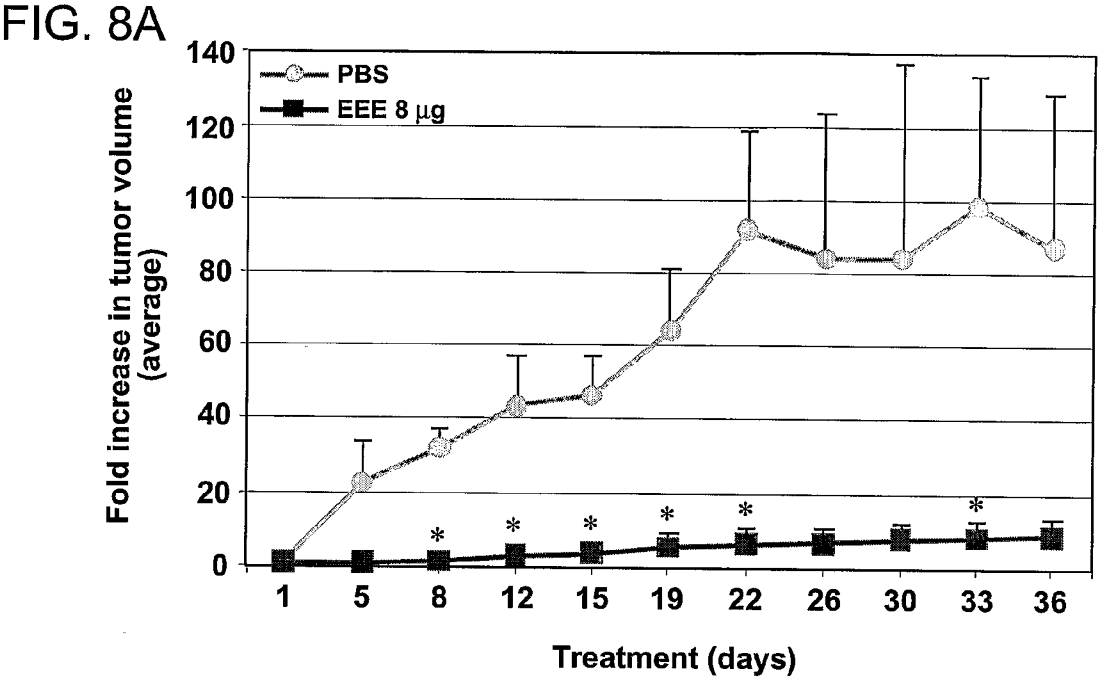
FIG. 8A-B show the effect of the EEE triple variant on the growth of DU145 xenograft in athymic mice.
Figure 8B:
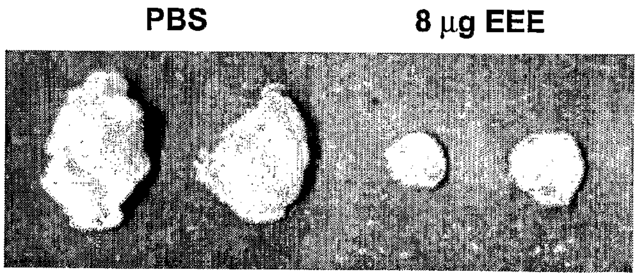

As the EEE variant exhibits the highest level of anti-angiogenic activity in a Matrigel plug assay, its effect on in vivo tumor xenograft model was next examined. For this aim, DU145 human prostate carcinoma cell suspension ($5\times10^6$ cells in 100 μl saline) was injected subcutaneously into the flank of 5 weeks old female athymic nude mice (CD-1). The tumors were allowed to grow for about 1 week after which mice were randomized by tumor volume into 2 groups. One group was injected intravenously with the EEE variant, 8 μg per injection (n=3). The other group was used as a control group and was injected intravenously with PBS (n=2). Tumor volume was calculated using a caliper by multiplying length× width×depth. All treatments were administered 3 times a week, and tumor volume was monitored twice a week. Results are presented as the average of fold increase in tumor volume per each group vs. its initial size. Student t-test was used to analyze statistical significance of the differences between average fold increase in tumor volume between the treated group and the control group (*P≦0.05). As shown in FIGS. 8A-B treatment of DU145 xenografts with the EEE variant significantly reduced tumor volume

Example 8

Generation of Anti-CK2 and Anti-PKA Phosphorylated PEDF Polyclonal Antibodies Anti-phospho-Ser24 (α-pSer24; CK2 site) PEDF polyclonal antibodies were generated in rabbits against a synthetic 16-mer peptide corresponding to amino acids 14-29 of human PEDF having the amino acid sequence: LGHSSCQNPAS(phospho)PPEEG set forth in SEQ ID NO:15. Anti-phospho-Ser227 (α-pSer227; PKA site) PEDF polyclonal antibodies were generated against a synthetic 15-mer peptide corresponding to amino acids 219-233 of human PEDF having the amino acid sequence: TKFDSRKTS(phospho)LEDFYL set forth in SEQ ID NO:16. In addition, anti-PEDF (α-PEDF) polyclonal antibodies were generated against a 17-mer peptide corresponding to amino acids 327-343 of human PEDF having the amino acid sequence: KSLQEMKLQSLFDSPDF set forth SEQ ID NO:17. The method for the preparation of the polyclonal antibodies is as known in the art (see Harlow and Lane (1988) Antibodies: A Laboratory Manual CSH Press, the content of which is incorporated by reference as if fully set forth herein).

Figure 9A:
FIG. 9A-C show the recognition of PEDF variants by anti-CK2- or anti-PKA-phosphorylated PEDF polyclonal antibodies.

To confirm that the polyclonal antibodies recognize PEDF, rPEDF and plPEDF were immunoblotted with the various anti-phospho-PEDF antibodies. As shown in FIG. 9A both proteins were recognized by αpSer24 and by αpSer227, however both antibodies recognized plPEDF to a higher extent as compared to rPEDF, and the recognition of plPEDF was more pronounced with αpSer24. These results confirm the observation disclosed herein above that PEDF in human plasma is present in the circulation as a phospho-protein, which is phosphorylated mainly on its CK2 sites.

Figure 9B:
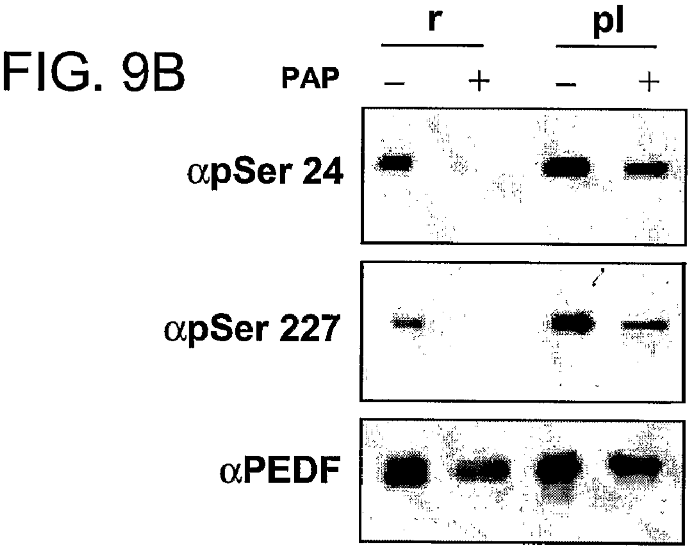
Figure 9C:
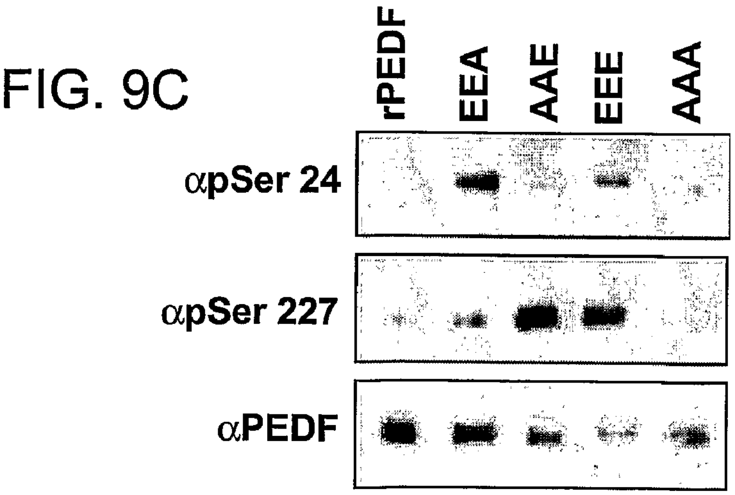

To further verify that the antibodies were indeed phosphorylated PEDF antibodies, rPEDF and plPEDF were treated with potato acid phosphatase as follows: rPEDF (1 μg) or plPEDF (1 μg) were incubated with potato acid phosphatase (PAP, 0.5 U) for 30 minutes at 37° C. Thereafter, the samples were subjected to immunoblotting with the various anti-phospho-PEDF antibodies. Phosphatase treatment of rPEDF completely abolished its recognition by both αpSer24 and by αpSer227, while the same treatment of plPEDF significantly reduced its recognition by the phosphorylated antibodies (FIG. 9B). Finally, the various PEDF variants (EEA, AAE, EEE and AAA) were subjected to immunoblotting with the anti-phospho-PEDF antibodies. As shown in FIG. 9C, interestingly αpSer24 antibody highly recognized the CK2 phosphorylated mutants (EEA and EEE) and the αpSer227 antibody highly recognized the PKA phosphorylated mutants (AAE and EEE).

It will be appreciated by persons skilled in the art that the present invention is not limited by what has been particularly shown and described herein above. Rather the scope of the invention is defined by the claims that follow.

The invention claimed is:

1. An isolated variant of pigment epithelium derived factor (PEDF), wherein the isolated variant differs from wild-type PEDF by having three serine residues 24, 114, and 227, the residues being numbered according to SEQ ID NO:1, substituted by amino acid residues selected from the group consisting of negatively charged amino acid residues and non polar amino acid residues, and wherein said variant has anti-angiogenic activity.

2. The isolated variant of PEDF according to claim 1 having neurotrophic activity.

3. The isolated variant of PEDF according to claim 2, wherein the three serine residues are substituted by negatively charged amino acid residues.

4. The isolated variant of PEDF according to claim 3 comprising the amino acid sequence as set forth in SEQ ID NO:2.

5. The isolated variant of PEDF according to claim 2, wherein serine 24 and serine 114 are substituted by non polar amino acid residues, and wherein serine 227 is substituted by an amino acid residue selected from the group consisting of negatively charged amino acid residues and non polar amino acid residues.

6. The isolated variant of PEDF according to claim 5 comprising an amino acid sequence selected from the group consisting of SEQ ID NO:3 and SEQ ID NO:4.

7. The isolated variant of PEDF according to claim 1 being essentially devoid of neurotrophic activity.

8. The isolated variant of PEDF according to claim 7, wherein serine 24 and serine 114 are substituted by negatively charged amino acid residues, and serine 227 is substituted by a non-polar amino acid residue.

9. The isolated variant of PEDF according to claim 8 comprising the amino acid sequence as set forth in SEQ ID NO:5.

10. An isolated polynucleotide sequence encoding an anti-angiogenic variant of pigment epithelium derived factor (PEDF) according to claim 1.

11. The isolated polynucleotide sequence according to claim 10, wherein the anti-angiogenic variant of PEDF has neurotrophic activity.

12. The isolated polynucleotide sequence according to claim 11, wherein the three serine residues are substituted by negatively charged amino acid residues.

13. The isolated polynucleotide sequence according to claim 12 comprising SEQ ID NO:7.

14. The isolated polynucleotide sequence according to claim 11, wherein serine 24 and serine 114 are substituted by non polar amino acid residues, and serine 227 is substituted by an amino acid residue selected from the group consisting of negatively charged amino acid residues and non polar amino acid residues.

15. The isolated polynucleotide sequence according to claim 14 selected from the group consisting of SEQ ID NO: 8 and SEQ ID NO:9.

16. The isolated polynucleotide sequence according to claim 10, wherein the anti-angiogenic variant of PEDF is essentially devoid of neurotrophic activity.

17. The isolated polynucleotide sequence to claim 16, wherein serine 24 and serine 114 are substituted by negatively charged amino acid residues and serine 227 is substituted by a non-polar amino acid residue.

18. The isolated polynucleotide sequence according to claim 17 comprising SEQ ID NO:10.

19. An expression vector comprising an isolated polynucleotide sequence encoding an anti-angiogenic variant of PEDF according to claim 10.

20. A pharmaceutical composition comprising as an active ingredient an expression vector comprising an isolated polynucleotide sequence encoding an anti-angiogenic variant of PEDF according to claim 19 and a pharmaceutically acceptable carrier.

21. A pharmaceutical composition comprising as an active ingredient an isolated polynucleotide sequence encoding an anti-angiogenic variant of PEDF according to claim 10 and a pharmaceutically acceptable carrier.

22. A pharmaceutical composition comprising as an active ingredient an isolated variant of PEDF according to claim 1 and a pharmaceutically acceptable carrier.

23. A method for treating a disease or disorder associated with neovascularization in a subject comprising administering to the subject in need thereof a therapeutically effective amount of a pharmaceutical composition according to claim 22, wherein the disease or disorder associated with neovascularization is selected from the group consisting of cancer and macular degeneration.

24. The method according to claim 23, wherein the cancer is selected from the group consisting of sarcoma, carcinoma, fibro sarcoma, myxo sarcoma, lipo sarcoma, chondro sarcoma, osteogenic sarcoma, chordoma, angiosarcoma, endothelio sarcoma, lymphangio sarcoma, lymphangioendothelio sarcoma, synovioma, mesothelioma, Ewing's tumor leiomydsarcoma, rhabdomyo sarcoma, colon carcinoma, pancreatic cancer, breast cancer, ovarian cancer, prostate cancer, squamous cell carcinoma, basal cell carcinoma, adenocarcinoma sweat gland carcinoma, sebaceous gland carcinoma, papillary carcinoma, papillary adenocarcinoma, cystadenocarcinoma, medullary carcinoma, bronchogenic carcinoma, renal cell carcinoma, hepatoma bile duct carcinoma, choriocarcinoma, seminoma, embryonal carcinoma, Wilms' tumor cervical cancer, testicular tumor, lung carcinoma, small cell lung carcinoma, bladder carcinoma, epithelial carcinoma, glioma, astrocytoma, medulloblastoma, craniopharyngioma, ependymoma, Kaposi's sarcoma, pinealoma, hemangioblastoma, acoustic neuroma, oligodendroglioma, menangioma, melanoma, and neuroblastoma.

25. A method for producing an anti-angiogenic variant of PEDF comprising culturing a host cell comprising an isolated polynucleotide encoding an anti-angiogenic variant of PEDF according to claim 1 under conditions promoting expression of the variant and recovering said variant.

26. The method according to claim 25, wherein the host cell is a eukaryotic cell.

* * * * *